(12) United States Patent
Freskgard et al.

(10) Patent No.: US 10,683,329 B2
(45) Date of Patent: Jun. 16, 2020

(54) DUAL-SITE BACE1 INHIBITORS

(71) Applicant: Hoffmann-La Roche Inc., Little Falls, NJ (US)

(72) Inventors: Per-Ola Freskgard, Renach BL (CH); Eric A. Kitas, Aesch (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/527,917

(22) PCT Filed: Nov. 25, 2015

(86) PCT No.: PCT/EP2015/077581
§ 371 (c)(1),
(2) Date: May 18, 2017

(87) PCT Pub. No.: WO2016/083425
PCT Pub. Date: Jun. 2, 2016

(65) Prior Publication Data
US 2018/0312541 A1 Nov. 1, 2018

(30) Foreign Application Priority Data
Nov. 28, 2014 (EP) .................................. 14195323

(51) Int. Cl.
| | | |
|---|---|---|
| A61K 38/08 | (2019.01) | |
| A61K 38/10 | (2006.01) | |
| A61K 38/41 | (2006.01) | |
| A61K 47/60 | (2017.01) | |
| A61K 47/66 | (2017.01) | |
| C07K 7/08 | (2006.01) | |
| C07K 14/81 | (2006.01) | |
| A61K 38/55 | (2006.01) | |
| A61K 47/65 | (2017.01) | |
| A61K 38/00 | (2006.01) | |

(52) U.S. Cl.
CPC ............... *C07K 7/08* (2013.01); *A61K 38/08* (2013.01); *A61K 38/10* (2013.01); *A61K 38/55* (2013.01); *A61K 47/60* (2017.08); *A61K 47/65* (2017.08); *C07K 14/8142* (2013.01); *A61K 38/00* (2013.01)

(58) Field of Classification Search
CPC ........ A61K 38/08; A61K 38/10; A61K 38/55; A61K 47/60; A61K 47/65; C07K 7/06; C07K 7/08; C07K 14/8142
See application file for complete search history.

(56) References Cited

U.S. PATENT DOCUMENTS

| | | | |
|---|---|---|---|
| 8,815,841 B2 * | 8/2014 | Hilpert | C07D 267/10 514/211.01 |
| 9,751,886 B2 * | 9/2017 | Oehlrich | A61K 31/4985 |
| 10,208,087 B2 * | 2/2019 | Freskgard | C07K 7/08 |
| 2007/0149763 A1 | 6/2007 | Komacker et al. | |
| 2008/0317767 A1 | 12/2008 | Braxmeier et al. | |

FOREIGN PATENT DOCUMENTS

| | | |
|---|---|---|
| WO | 2005097199 A1 | 10/2005 |
| WO | 2013056054 A2 | 4/2013 |

OTHER PUBLICATIONS

Schieb et al. Structural Design, Solid-Phase Synthesis and Activity of Membrane-Anchored Beta-Secretase Inhibitors on A-beta Generation from Wild-Type and Swedish-Mutant APP. Chemistry: A European Journal. 2010, vol. 16, pp. 14412-14423. (Year: 2010).*
The International Search Report and Written Opinion, dated Feb. 8, 2016, in the related PCT Application No. PCT/EP2015/077581.
Linning et al., "Optimisation of BACE1 inhibition of thripartite structures by modification of membrane anchors, spacers and pharmacophores—development of potential agents for the treatment of Alzheimer's disease" Organic & Biomolecular Chemistry, 10(41), p. 8216, Jan. 1, 2012.
The English translation of the Japanese Office Action, dated Jul. 16, 2019, in the related Japanese Appl. No. 2017-528479.
Komacker et al., "An inhibitor binding pocket distinct from the catalytic active site on human beta-APP cleaving anzyme," Biochemistry. Aug. 30, 2005;44(34):11567-73.

* cited by examiner

*Primary Examiner* — Jeffrey E. Russel

(57) ABSTRACT

Provided herein are peptides having dual-site BACE1 inhibitory activity, useful for the treatment of, for example Alzheimer's disease and diabetes. One such peptide is a dual-site BACE1 inhibitor, or a pharmaceutically acceptable salt thereof, binding to both an enzymatic active site and an catalytic domain of the BACE enzyme, and an exosite inhibitory part is connected to an active-site inhibitory part of the dual site BACE1 inhibitor by a linker.

15 Claims, No Drawings
Specification includes a Sequence Listing.

```
                      SEQUENCE LISTING

<160> NUMBER OF SEQ ID NOS: 111

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (13)..(13)
<223> OTHER INFORMATION: Statine
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (18)..(18)
<223> OTHER INFORMATION: Lys(Chol)

<400> SEQUENCE: 1

Tyr Pro Tyr Phe Ile Pro Leu Gly Gly Glu Val Asn Xaa Val Ala Glu
1               5                   10                  15

Pro Lys

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 2

Tyr Pro Tyr Phe Ile Pro Leu Gly Gly Gly Glu Val Asn Xaa Val Ala
```

```
1               5                   10                  15

Glu Pro Lys

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<223> OTHER INFORMATION: N-term Ac
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 3

Tyr Pro Tyr Phe Ile Pro Leu Gly Gly Gly Glu Val Asn Xaa Val Ala
1               5                   10                  15

Glu Pro Lys

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 4

Tyr Pro Tyr Phe Ile Pro Leu Gly Gly Gly Glu Val Asn Xaa Asp Ala
1               5                   10                  15

Glu Pro Lys

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (15)..(15)
<223> OTHER INFORMATION: Statine
<220> FEATURE:
<221> NAME/KEY: MOD_RES
<222> LOCATION: (19)..(19)
<223> OTHER INFORMATION: D-amino acid
<220> FEATURE:
```

```
<221> NAME/KEY: MOD_RES
<222> LOCATION: (20)..(20)
<223> OTHER INFORMATION: Lys(Chol)

<400> SEQUENCE: 5

Tyr Pro Tyr Phe Ile Pro Leu Gly Gly Gly Gly Glu Val Asn Xaa Val
1               5                   10                  15

Ala Glu Pro Lys
        20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (15)..(15)
<223> OTHER INFORMATION: Statine
<220> FEATURE:
<221> NAME/KEY: MOD_RES
<222> LOCATION: (19)..(19)
<223> OTHER INFORMATION: D-amino acid
<220> FEATURE:
<221> NAME/KEY: MOD_RES
<222> LOCATION: (20)..(20)
<223> OTHER INFORMATION: Lys(Chol)

<400> SEQUENCE: 6

Tyr Pro Tyr Phe Ile Pro Leu Gly Gly Gly Gly Glu Val Asn Xaa Asp
1               5                   10                  15

Ala Glu Pro Lys
        20

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (16)..(16)
<223> OTHER INFORMATION: Statine
<220> FEATURE:
<221> NAME/KEY: MOD_RES
<222> LOCATION: (20)..(20)
<223> OTHER INFORMATION: D-amino acid
<220> FEATURE:
<221> NAME/KEY: MOD_RES
<222> LOCATION: (21)..(21)
<223> OTHER INFORMATION: Lys(Chol)

<400> SEQUENCE: 7

Tyr Pro Tyr Phe Ile Pro Leu Gly Gly Gly Gly Gly Glu Val Asn Xaa
1               5                   10                  15

Val Ala Glu Pro Lys
            20

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide
```

```
<400> SEQUENCE: 8

Tyr Pro Tyr Phe Ile Pro Leu
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 9

Tyr Pro Tyr Phe Ile Pro Leu
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 10

Tyr Pro Tyr Phe Ile Pro Leu
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 11

Tyr Pro Tyr Phe Ile Pro Leu
1               5

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (17)..(17)
<223> OTHER INFORMATION: Statine
<220> FEATURE:
<221> NAME/KEY: MOD_RES
<222> LOCATION: (21)..(21)
<223> OTHER INFORMATION: D-amino acid
<220> FEATURE:
<221> NAME/KEY: MOD_RES
<222> LOCATION: (22)..(22)
<223> OTHER INFORMATION: Lys(Chol)

<400> SEQUENCE: 12

Tyr Pro Tyr Phe Ile Pro Leu Gly Gly Gly Gly Gly Gly Glu Val Asn
1               5                   10                  15

Xaa Val Ala Glu Pro Lys
            20

<210> SEQ ID NO 13
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 13

Tyr Pro Tyr Phe Ile Pro Leu
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 14

Tyr Pro Tyr Phe Ile Pro Leu
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<223> OTHER INFORMATION: N-term Ac

<400> SEQUENCE: 15

Tyr Pro Tyr Phe Ile Pro Leu
1               5

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 16

Leu Ile Tyr Phe Pro Tyr Pro Gly Gly Gly Glu Val Asn Xaa Val Ala
1               5                   10                  15

Glu Pro Lys

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
```

```
<222> LOCATION: (15)..(15)
<223> OTHER INFORMATION: Statine
<220> FEATURE:
<221> NAME/KEY: MOD_RES
<222> LOCATION: (19)..(19)
<223> OTHER INFORMATION: D-amino acid
<220> FEATURE:
<221> NAME/KEY: MOD_RES
<222> LOCATION: (20)..(20)
<223> OTHER INFORMATION: Lys(Chol)

<400> SEQUENCE: 17

Leu Ile Tyr Phe Pro Tyr Pro Gly Gly Gly Gly Glu Val Asn Xaa Val
1               5                   10                  15

Ala Glu Pro Lys
            20

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(C12)

<400> SEQUENCE: 18

Tyr Pro Tyr Phe Ile Pro Leu Gly Gly Gly Glu Val Asn Xaa Val Ala
1               5                   10                  15

Glu Pro Lys

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(C14)

<400> SEQUENCE: 19

Tyr Pro Tyr Phe Ile Pro Leu Gly Gly Gly Glu Val Asn Xaa Val Ala
1               5                   10                  15

Glu Pro Lys

<210> SEQ ID NO 20
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(27-OH-Chol)

<400> SEQUENCE: 20

Tyr Pro Tyr Phe Ile Pro Leu Gly Gly Gly Glu Val Asn Xaa Val Ala
1               5                   10                  15

Glu Pro Lys

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol-27-TFA-ester)

<400> SEQUENCE: 21

Tyr Pro Tyr Phe Ile Pro Leu Gly Gly Gly Glu Val Asn Xaa Val Ala
1               5                   10                  15

Glu Pro Lys

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 22
```

Tyr Pro Tyr Phe Ile Pro Leu Gly Lys Gly Glu Val Asn Xaa Val Ala
1               5                   10                  15

Glu Pro Lys

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (19)..(19)
<223> OTHER INFORMATION: Lys(Chol)

<400> SEQUENCE: 23

Tyr Pro Tyr Phe Ile Pro Leu Gly Gly Gly Glu Val Asn Xaa Val Ala
1               5                   10                  15

Glu Phe Lys

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (15)..(15)
<223> OTHER INFORMATION: (3S,4S)-4-amino-3-hydroxy-6-methylthiohexanoic
      acid
<220> FEATURE:
<221> NAME/KEY: MOD_RES
<222> LOCATION: (19)..(19)
<223> OTHER INFORMATION: D-amino acid
<220> FEATURE:
<221> NAME/KEY: MOD_RES
<222> LOCATION: (20)..(20)
<223> OTHER INFORMATION: Lys(Chol)

<400> SEQUENCE: 24

Tyr Pro Tyr Phe Ile Pro Leu Gly Gly Gly Gly Glu Val Asn Xaa Val
1               5                   10                  15

Ala Glu Phe Lys
            20

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (16)..(16)
<223> OTHER INFORMATION: (3S,4S)-4-amino-3-hydroxy-6-methylthiohexanoic
      acid
<220> FEATURE:
<221> NAME/KEY: MOD_RES
<222> LOCATION: (20)..(20)
<223> OTHER INFORMATION: D-amino acid
<220> FEATURE:
<221> NAME/KEY: MOD_RES
<222> LOCATION: (21)..(21)

```
<223> OTHER INFORMATION: Lys(Chol)

<400> SEQUENCE: 25

Tyr Pro Tyr Phe Ile Pro Leu Gly Gly Gly Gly Gly Glu Val Asn Xaa
1               5                   10                  15

Val Ala Glu Phe Lys
            20

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 26

Tyr Pro Tyr Phe Ile Pro Leu
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 27

Tyr Pro Tyr Phe Ile Pro Leu
1               5

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: (3S,4S)-4-amino-3-hydroxy-6-methylthiohexanoic
      acid
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(C14)

<400> SEQUENCE: 28

Tyr Pro Tyr Phe Ile Pro Leu Gly Gly Gly Glu Val Asn Xaa Val Ala
1               5                   10                  15

Glu Phe Lys

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MISC_FEATURE
<222> LOCATION: (14)..(15)
<223> OTHER INFORMATION: "Tang" hydroxyethylene dipeptide isostere
```

```
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 29

Tyr Pro Tyr Phe Ile Pro Leu Gly Gly Gly Glu Val Asn Leu Ala Ala
1               5                   10                  15

Glu Pro Lys

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ether')

<400> SEQUENCE: 30

Tyr Pro Tyr Phe Ile Pro Leu Gly Gly Gly Glu Val Asn Xaa Val Ala
1               5                   10                  15

Glu Pro Lys

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 31

Tyr Pro Lys Phe Ile Pro Leu Gly Gly Gly Glu Val Asn Xaa Val Ala
1               5                   10                  15

Glu Pro Lys

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
```

```
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 32

Tyr Pro Tyr Phe Lys Pro Leu Gly Gly Gly Glu Val Asn Xaa Val Ala
1               5                   10                  15

Glu Pro Lys

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 33

Tyr Pro Tyr Phe Ile Lys Leu Gly Gly Gly Glu Val Asn Xaa Val Ala
1               5                   10                  15

Glu Pro Lys

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 34

Tyr Pro Tyr Phe Lys Pro Leu
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 35

Tyr Pro Tyr Phe Ile Lys Leu
1               5

<210> SEQ ID NO 36
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 36

Tyr Pro Lys Phe Ile Pro Leu Gly Lys Gly Glu Val Asn Xaa Val Ala
1               5                   10                  15

Glu Pro Lys

<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 37

Tyr Pro Tyr Phe Lys Pro Leu Gly Lys Gly Glu Val Asn Xaa Val Ala
1               5                   10                  15

Glu Pro Lys

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
```

```
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 38

Tyr Pro Tyr Phe Ile Lys Leu Gly Lys Gly Glu Val Asn Xaa Val Ala
1               5                   10                  15

Glu Pro Lys

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 39

Tyr Pro Tyr Phe Ile Pro Leu Gly Lys Gly Glu Val Asn Xaa Val Ala
1               5                   10                  15

Glu Pro Lys

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 40

Tyr Pro Tyr Phe Ile Pro Leu Lys Gly Gly Glu Val Asn Xaa Val Ala
1               5                   10                  15

Glu Pro Lys

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
```

```
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 41

Tyr Pro Tyr Phe Ile Pro Leu Lys Gly Gly Glu Val Asn Xaa Val Ala
1               5                   10                  15

Glu Pro Lys

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 42

Tyr Pro Tyr Phe Ile Pro Leu Gly Gly Lys Glu Val Asn Xaa Val Ala
1               5                   10                  15

Glu Pro Lys

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (10)..(10)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 43
```

Tyr Pro Tyr Phe Ile Pro Leu Gly Gly Lys Glu Val Asn Xaa Val Ala
1               5                   10                  15

Glu Pro Lys

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ether')

<400> SEQUENCE: 44

Tyr Pro Lys Phe Ile Pro Leu Gly Lys Gly Glu Val Asn Xaa Val Ala
1               5                   10                  15

Glu Pro Lys

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 45

Tyr Pro Lys Phe Lys Pro Leu Gly Lys Gly Glu Val Asn Xaa Val Ala
1               5                   10                  15

Glu Pro Lys

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES

```
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 46

Tyr Pro Lys Phe Ile Lys Leu Gly Lys Gly Glu Val Asn Xaa Val Ala
1               5                   10                  15

Glu Pro Lys

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol)

<400> SEQUENCE: 47

Tyr Pro Lys Phe Lys Lys Leu Gly Lys Gly Glu Val Asn Xaa Val Ala
1               5                   10                  15

Glu Pro Lys

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')
```

-continued

<400> SEQUENCE: 48

Lys Pro Tyr Phe Ile Pro Leu Gly Lys Gly Glu Val Asn Xaa Val Ala
1               5                   10                  15

Glu Pro Lys

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 49

Tyr Lys Tyr Phe Ile Pro Leu Gly Lys Gly Glu Val Asn Xaa Val Ala
1               5                   10                  15

Glu Pro Lys

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 50

Tyr Pro Tyr Lys Ile Pro Leu Gly Lys Gly Glu Val Asn Xaa Val Ala
1               5                   10                  15

Glu Pro Lys

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide

```
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 51

Tyr Pro Tyr Phe Ile Pro Lys Gly Lys Gly Glu Val Asn Xaa Val Ala
1               5                   10                  15

Glu Pro Lys

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 52

Tyr Pro Tyr Phe Ile Pro Leu Ala Gly Gly Glu Val Asn Xaa Val Ala
1               5                   10                  15

Glu Pro Lys

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
```

```
<223> OTHER INFORMATION: Lys(Chol'ester')

<400> SEQUENCE: 53

Tyr Pro Tyr Phe Ile Pro Leu Gly Ala Gly Glu Val Asn Xaa Val Ala
1               5                   10                  15

Glu Pro Lys

<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 54

Tyr Pro Tyr Phe Ile Pro Leu Ser Gly Gly Glu Val Asn Xaa Val Ala
1               5                   10                  15

Glu Pro Lys

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 55

Lys Pro Tyr Phe Ile Pro Leu Gly Lys Gly Glu Val Asn Xaa Val Ala
1               5                   10                  15

Glu Pro Lys

<210> SEQ ID NO 56
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      modified peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 56

Tyr Lys Tyr Phe Ile Pro Leu Gly Lys Gly Glu Val Asn Xaa Val Ala
1               5                   10                  15

Glu Pro Lys

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 57

Tyr Pro Lys Phe Ile Pro Leu Gly Lys Gly Glu Val Asn Xaa Val Ala
1               5                   10                  15

Glu Pro Lys

<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (4)..(4)
<223> OTHER INFORMATION: D-amino acid
<220> FEATURE:
```

```
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 58

Tyr Pro Tyr Lys Ile Pro Leu Gly Lys Gly Glu Val Asn Xaa Val Ala
1               5                   10                  15

Glu Pro Lys

<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 59

Tyr Pro Tyr Phe Lys Pro Leu Gly Lys Gly Glu Val Asn Xaa Val Ala
1               5                   10                  15

Glu Pro Lys

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (6)..(6)
<223> OTHER INFORMATION: D-amino acid
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
```

```
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 60

Tyr Pro Tyr Phe Ile Lys Leu Gly Lys Gly Glu Val Asn Xaa Val Ala
1               5                   10                  15

Glu Pro Lys

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (7)..(7)
<223> OTHER INFORMATION: D-amino acid
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 61

Tyr Pro Tyr Phe Ile Pro Lys Gly Lys Gly Glu Val Asn Xaa Val Ala
1               5                   10                  15

Glu Pro Lys

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      modified peptide, acids 2-11 in brackets
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (15)..(15)
<223> OTHER INFORMATION: Statine
<220> FEATURE:
<221> NAME/KEY: MOD_RES
<222> LOCATION: (19)..(19)
<223> OTHER INFORMATION: D-amino acid
<220> FEATURE:
<221> NAME/KEY: MOD_RES
<222> LOCATION: (20)..(20)
<223> OTHER INFORMATION: Lys(Chol'ester')

<400> SEQUENCE: 62
```

```
Lys Gly Lys Gly Leu Pro Ile Phe Tyr Pro Tyr Glu Val Asn Xaa Val
1               5                   10                  15

Ala Glu Pro Lys
            20

<210> SEQ ID NO 63
<211> LENGTH: 20
<212> TYPE: PRT
<213> ORGANISM: Artificial Sequence
<220> FEATURE:
<223> OTHER INFORMATION: Description of Artificial Sequence: Synthetic
      modified peptide, acids 2-11 in brackets
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (15)..(15)
<223> OTHER INFORMATION: Statine
<220> FEATURE:
<221> NAME/KEY: MOD_RES
<222> LOCATION: (19)..(19)
<223> OTHER INFORMATION: D-amino acid
<220> FEATURE:
<221> NAME/KEY: MOD_RES
<222> LOCATION: (20)..(20)
<223> OTHER INFORMATION: Lys(Chol'ester')

<400> SEQUENCE: 63

Lys Gly Lys Gly Leu Pro Ile Phe Tyr Pro Tyr Glu Val Asn Xaa Val
1               5                   10                  15

Ala Glu Pro Lys
            20

<210> SEQ ID NO 64
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: (3S,4S)-4-amino-3-hydroxy-6-methylthiohexanoic
      acid
<220> FEATURE:
<221> NAME/KEY: MOD_RES
<222> LOCATION: (19)..(19)
<223> OTHER INFORMATION: Lys(Chol'ester')

<400> SEQUENCE: 64

Tyr Pro Lys Phe Ile Pro Leu Gly Lys Gly Glu Val Asn Xaa Val Ala
1               5                   10                  15

Glu Pro Lys

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
```

```
    modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MISC_FEATURE
<222> LOCATION: (14)..(15)
<223> OTHER INFORMATION: "Tang" hydroxyethylene dipeptide isostere
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 65

Tyr Pro Lys Phe Ile Pro Leu Gly Lys Gly Glu Val Asn Leu Ala Ala
1               5                   10                  15

Glu Pro Lys

<210> SEQ ID NO 66
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 66

Tyr Pro Tyr Phe Lys Pro Ala Gly Lys Gly Glu Val Asn Xaa Val Ala
1               5                   10                  15

Glu Pro Lys

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
```

-continued

```
<222> LOCATION: (19)..(19)
<223> OTHER INFORMATION: Lys(Chol'ester')

<400> SEQUENCE: 67

Thr Phe Lys Pro Ala Asn Gly Gly Lys Gly Glu Val Asn Xaa Val Ala
1               5                   10                  15
Glu Pro Lys

<210> SEQ ID NO 68
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 68

Gly Ala Arg Phe Ile Pro Ala Gly Lys Gly Glu Val Asn Xaa Val Ala
1               5                   10                  15
Glu Pro Lys

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 69

Tyr Pro Lys Phe Ile Pro Ala Gly Lys Gly Glu Val Asn Xaa Val Ala
1               5                   10                  15
Glu Pro Lys

<210> SEQ ID NO 70
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      modified peptide
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (14)..(14)
<223> OTHER INFORMATION: Statine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: Lys(Chol'ester')

<400> SEQUENCE: 70

Tyr Pro Lys Phe Ile Ser Ala Gly Lys Gly Glu Val Asn Xaa Val Ala
1               5                   10                  15

Glu Pro Lys

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 71

Tyr Pro Tyr Phe Ile Pro Leu
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<223> OTHER INFORMATION: N-term Ac

<400> SEQUENCE: 72

Tyr Pro Tyr Phe Ile Pro Leu
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 73

Leu Ile Tyr Phe Pro Tyr Pro
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide
```

```
<400> SEQUENCE: 74

Tyr Pro Lys Phe Ile Pro Leu
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 75

Tyr Pro Tyr Phe Lys Pro Leu
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 76

Tyr Pro Tyr Phe Ile Lys Leu
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 77

Tyr Pro Lys Phe Lys Pro Leu Gly
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 78

Tyr Pro Lys Phe Ile Lys Leu
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 79

Tyr Pro Lys Phe Lys Lys Leu
1               5

<210> SEQ ID NO 80
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 80

Lys Pro Tyr Phe Ile Pro Leu
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 81

Tyr Lys Tyr Phe Ile Pro Leu
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 82

Tyr Pro Tyr Lys Ile Pro Leu
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 83

Tyr Pro Tyr Phe Ile Pro Lys
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (1)..(1)
<223> OTHER INFORMATION: D-amino acid

<400> SEQUENCE: 84

Lys Pro Tyr Phe Ile Pro Leu
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide
```

```
<220> FEATURE:
<221> NAME/KEY: MOD_RES
<222> LOCATION: (2)..(2)
<223> OTHER INFORMATION: D-amino acid

<400> SEQUENCE: 85

Tyr Lys Tyr Phe Ile Pro Leu
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (3)..(3)
<223> OTHER INFORMATION: D-amino acid

<400> SEQUENCE: 86

Tyr Pro Lys Phe Ile Pro Leu
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (4)..(4)
<223> OTHER INFORMATION: D-amino acid

<400> SEQUENCE: 87

Tyr Pro Tyr Lys Ile Pro Leu
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (5)..(5)
<223> OTHER INFORMATION: D-amino acid

<400> SEQUENCE: 88

Tyr Pro Tyr Phe Lys Pro Leu
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (6)..(6)
<223> OTHER INFORMATION: D-amino acid

<400> SEQUENCE: 89
```

```
Tyr Pro Tyr Phe Ile Lys Leu
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (7)..(7)
<223> OTHER INFORMATION: D-amino acid

<400> SEQUENCE: 90

Tyr Pro Tyr Phe Ile Pro Lys
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 91

Tyr Pro Tyr Phe Lys Pro Ala
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 92

Thr Phe Lys Pro Ala Asn Gly
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 93

Gly Ala Arg Phe Ile Pro Ala
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 94

Tyr Pro Lys Phe Ile Pro Ala
1               5

<210> SEQ ID NO 95
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      modified peptide

<400> SEQUENCE: 95

Tyr Pro Lys Phe Ile Ser Ala
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (4)..(4)
<223> OTHER INFORMATION: Statine
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (9)..(9)
<223> OTHER INFORMATION: Lys(Chol)

<400> SEQUENCE: 96

Glu Val Asn Xaa Val Ala Glu Pro Lys
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (4)..(4)
<223> OTHER INFORMATION: Statine
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (9)..(9)
<223> OTHER INFORMATION: Lys(Chol)

<400> SEQUENCE: 97

Glu Val Asn Xaa Asp Ala Glu Pro Lys
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (4)..(4)
<223> OTHER INFORMATION: Statine
<220> FEATURE:
<221> NAME/KEY: MOD_RES
<222> LOCATION: (8)..(8)
```

```
<223> OTHER INFORMATION: D-amino acid
<220> FEATURE:
<221> NAME/KEY: MOD_RES
<222> LOCATION: (9)..(9)
<223> OTHER INFORMATION: Lys(C12)

<400> SEQUENCE: 98

Glu Val Asn Xaa Val Ala Glu Pro Lys
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (4)..(4)
<223> OTHER INFORMATION: Statine
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (9)..(9)
<223> OTHER INFORMATION: Lys(C14)

<400> SEQUENCE: 99

Glu Val Asn Xaa Val Ala Glu Pro Lys
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (4)..(4)
<223> OTHER INFORMATION: Statine
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (9)..(9)
<223> OTHER INFORMATION: Lys(27-OH-Chol)

<400> SEQUENCE: 100

Glu Val Asn Xaa Val Ala Glu Pro Lys
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (4)..(4)
<223> OTHER INFORMATION: Statine
<220> FEATURE:
<221> NAME/KEY: MOD_RES
<222> LOCATION: (8)..(8)
<223> OTHER INFORMATION: D-amino acid
```

```
<220> FEATURE:
<221> NAME/KEY: MOD_RES
<222> LOCATION: (9)..(9)
<223> OTHER INFORMATION: Lys(Chol-27-TFA-ester)

<400> SEQUENCE: 101

Glu Val Asn Xaa Val Ala Glu Pro Lys
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (4)..(4)
<223> OTHER INFORMATION: Statine
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (9)..(9)
<223> OTHER INFORMATION: Lys(Chol'ester')

<400> SEQUENCE: 102

Glu Val Asn Xaa Val Ala Glu Pro Lys
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (4)..(4)
<223> OTHER INFORMATION: Statine
<220> FEATURE:
<221> NAME/KEY: MOD_RES
<222> LOCATION: (9)..(9)
<223> OTHER INFORMATION: Lys(Chol)

<400> SEQUENCE: 103

Glu Val Asn Xaa Val Ala Glu Phe Lys
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (4)..(4)
<223> OTHER INFORMATION: (3S,4S)-4-amino-3-hydroxy-6-methylthiohexanoic
      acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (9)..(9)
<223> OTHER INFORMATION: Lys(Chol)
```

```
<400> SEQUENCE: 104

Glu Val Asn Xaa Val Ala Glu Phe Lys
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (4)..(4)
<223> OTHER INFORMATION: (3S,4S)-4-amino-3-hydroxy-6-methylthiohexanoic
      acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (9)..(9)
<223> OTHER INFORMATION: Lys(C14)

<400> SEQUENCE: 105

Glu Val Asn Xaa Val Ala Glu Phe Lys
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MISC_FEATURE
<222> LOCATION: (4)..(5)
<223> OTHER INFORMATION: "Tang" hydroxyethylene dipeptide isostere
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (9)..(9)
<223> OTHER INFORMATION: Lys(Chol)

<400> SEQUENCE: 106

Glu Val Asn Leu Ala Ala Glu Pro Lys
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (4)..(4)
<223> OTHER INFORMATION: Statine
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (9)..(9)
<223> OTHER INFORMATION: Lys(Chol'ether')
```

-continued

```
<400> SEQUENCE: 107

Glu Val Asn Xaa Val Ala Glu Pro Lys
1               5

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (11)..(11)
<223> OTHER INFORMATION: Statine
<220> FEATURE:
<221> NAME/KEY: MOD_RES
<222> LOCATION: (15)..(15)
<223> OTHER INFORMATION: D-amino acid
<220> FEATURE:
<221> NAME/KEY: MOD_RES
<222> LOCATION: (16)..(16)
<223> OTHER INFORMATION: Lys(Chol'ester')

<400> SEQUENCE: 108

Leu Pro Ile Phe Tyr Pro Tyr Glu Val Asn Xaa Val Ala Glu Pro Lys
1               5                   10                  15

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MOD_RES
<222> LOCATION: (4)..(4)
<223> OTHER INFORMATION: (3S,4S)-4-amino-3-hydroxy-6-methylthiohexanoic
      acid
<220> FEATURE:
<221> NAME/KEY: MOD_RES
<222> LOCATION: (9)..(9)
<223> OTHER INFORMATION: Lys(Chol'ester')

<400> SEQUENCE: 109

Glu Val Asn Xaa Val Ala Glu Pro Lys
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      modified peptide
<220> FEATURE:
<221> NAME/KEY: MISC_FEATURE
<222> LOCATION: (4)..(5)
<223> OTHER INFORMATION: "Tang" hydroxyethylene dipeptide isostere
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (9)..(9)
<223> OTHER INFORMATION: Lys(Chol'ester')

<400> SEQUENCE: 110

Glu Val Asn Leu Ala Ala Glu Pro Lys
```

```
<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: This sequence may encompass 2-6 residues

<400> SEQUENCE: 111

Gly Gly Gly Gly Gly Gly
1               5
```

DUAL-SITE BACE1 INHIBITORS

CROSS-REFERENCE TO RELATED APPLICATIONS

This application is a National Stage Application of PCT/EP2015/077581 filed Nov. 25, 2015, which claims priority from European Patent Application No. 14195323.2, filed on Nov. 28, 2014. The priority of both said PCT and European Patent Application are claimed.

SEQUENCE LISTING

The instant application contains a Sequence Listing which has been submitted electronically in ASCII format and is hereby incorporated by reference in its entirety. Said ASCII copy, created on Nov. 20, 2018, is named 036844-94967_(P32145-US)_SL.txt and is 47,986 bytes in size.

The present invention is concerned with peptides having dual BACE1 inhibitory properties, their manufacture, pharmaceutical compositions containing them and their use as therapeutically active substances.

Technical Field

The present compounds have Asp2 (β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or β-amyloid plaques and further deposits, particularly Alzheimer's disease.

BACKGROUND ART

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

The BACE1 enzyme is responsible for one of the proteolytic cleavages of the APP protein that contributes to the generation of the Alzheimer's disease-associated Aβ-peptide. Retarding or stopping the production of Aβ-peptide through inhibition of the BACE1 enzyme is a promising therapeutic concept.

Active site-directed BACE1 inhibitors are described in e.g. WO2006/002907 and exosite-directed (catalytic domain) BACE1 inhibitors are described in e.g. Kornacker et al., Biochemistry 2005, 44, 11567-73.

Bodor et al describe modified peptides suitable to penetrate the blood-brain-barrier (Bodor et al., Science, Vol. 257, 1992).

DETAILED DESCRIPTION OF THE INVENTION

Object of the present invention is dual-site BACE1 inhibitor, binding to both, the enzymatic active site and the catalytic domain of the BACE enzyme, the preparation of the above mentioned compounds, medicaments containing them and their manufacture as well as the use of the above mentioned compounds in the therapeutic and/or prophylactic treatment of diseases and disorders which are associated with inhibition of BACE1 activity, such as Alzheimer's disease. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

TABLE 1 amino acid abbreviations used herein

| Amino Acid | 3-Letter | 1-Letter |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Table 1: amino acid abbreviations used herein

The term "Sta" stands for statine, (3S,4S)-4-amino-3-hydroxy-6-methylheptanoic acid (CAS 49642-07-1).

The term "MetSta" stands for (3S,4S)-4-amino-3-hydroxy-6-methylthiohexanoic acid (CAS n/a), (CAS of Fmoc protected: 268542-18-3).

The term "27-OH-Chol" stands for 27-hydroxycholesterol (CAS 20380-11-4). Structure and preparation see page 18, compound 4.

The term "Chol-27-TFA-ester" stands for succinamic acid (3S,8S,9S,10R,13R,14S,17R)-17-[(1R,5R)-1,5-dimethyl-6-(2,2,2-trifluoro-acetoxy)-hexyl]-10,13-dimethyl-2,3,4,7,8,9,10,11,12,13,14,15,16,17-tetradecahydro-1H-cyclopenta[a]phenanthren-3-yl ester, this occurred as byproduct during TFA cleavage of "27-OH-Chol"-peptides.

The term "Chol'ester'" stands for cholesteryl hemisuccinate (CAS: 1510-21-0).

The term "PEG(3)" stands for 12-amino-4,7,10-trioxadodecanoic acid (CAS: 784105-33-5).

The term "PEG(4)" stands for 15-amino-4,7,10,13,tetraoxapentadecanoic acid (CAS: n/a), (CAS of Fmoc protected: 557756-85-1).

The term Leu*Ala stands for the "Tang" hydroxyethylene dipeptide isostere (reference: A. K. Ghosh, D. Shin, D. Downs, G. Koelsch, X. Lin, J. Ermolieff and J. Tang, *J. Am. Chem. Soc.*, 2000, 122, 3522)

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid (TFA) and the like. A specific salt is trifluoroacetate.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (–log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (–log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The invention also provides pharmaceutical compositions, methods of using, and methods of preparing the aforementioned compounds.

All separate embodiments may be combined.

Present invention relates to a dual-site BACE1 inhibitor, binding to both, the enzymatic active site and the catalytic domain of the BACE1 enzyme.

A certain embodiment of the invention relates to a dual-site BACE1 inhibitor according to claim 1, whereby the exosite inhibitory part (A') is connected to the active-site inhibitory part (B') of said BACE1 inhibitor by a linker (L'), or a pharmaceutically acceptable salt thereof.

A certain embodiment of the invention relates to a dual-site BACE1 inhibitor as described herein, wherein L' is selected from the group consisting of
  i. -(Gly)$_x$-, wherein x is 2, 3, 4, 5 or 6 (SEQ ID NO: 111),
  ii. —NH(CH$_2$)$_y$CO—, wherein y is 2, 4, 5 or 10,
  iii. PEG(3),
  iv. PEG(4),
  v. —X-Gly-Gly-, wherein X is selected from the group consisting of Ala, DAla, Ser, Lys and DLys,
  vi. -Gly-X-Gly-, wherein X is selected from the group consisting of Ala, DAla, Ser, Lys and DLys,
  vii. -Gly-Gly-X—, wherein X is selected from the group consisting of Ala, DAla, Ser, Lys and DLys, A certain embodiment of the invention relates to a dual-site BACE1 inhibitor as described herein, wherein A' is selected from the group consisting of
  i. Tyr-Pro-Tyr-Phe-Ile-Pro-Leu- (SEQ ID NO: 71),
  ii. Ac-Tyr-Pro-Tyr-Phe-Ile-Pro-Leu- (SEQ ID NO: 72),
  iii. Leu-Ile-Tyr-Phe-Pro-Tyr-Pro- (SEQ ID NO: 73),
  iv. Tyr-Pro-Lys-Phe-Ile-Pro-Leu- (SEQ ID NO: 74),
  v. Tyr-Pro-Tyr-Phe-Lys-Pro-Leu- (SEQ ID NO: 75),
  vi. Tyr-Pro-Tyr-Phe-Ile-Lys-Leu- (SEQ ID NO: 76),
  vii. Tyr-Pro-Lys-Phe-Lys-Pro-Leu-Gly- (SEQ ID NO: 77),
  viii. Tyr-Pro-Lys-Phe-Ile-Lys-Leu- (SEQ ID NO: 78).
  ix. Tyr-Pro-Lys-Phe-Lys-Lys-Leu- (SEQ ID NO: 79),
  x. Lys-Pro-Tyr-Phe-Ile-Pro-Leu- (SEQ ID NO: 80),
  xi. Tyr-Lys-Tyr-Phe-Ile-Pro-Leu- (SEQ ID NO: 81),
  xii. Tyr-Pro-Tyr-Lys-Ile-Pro-Leu- (SEQ ID NO: 82),
  xiii. Tyr-Pro-Tyr-Phe-Ile-Pro-Lys- (SEQ ID NO: 83),
  xiv. DLys-Pro-Tyr-Phe-Ile-Pro-Leu- (SEQ ID NO: 84),
  xv. Tyr-DLys-Tyr-Phe-Ile-Pro-Leu- (SEQ ID NO: 85),
  xvi. Tyr-Pro-DLys-Phe-Ile-Pro-Leu- (SEQ ID NO: 86),
  xvii. Tyr-Pro-Tyr-DLys-Ile-Pro-Leu- (SEQ ID NO: 87),
  xviii. Tyr-Pro-Tyr-Phe-DLys-Pro-Leu- (SEQ ID NO: 88),
  xix. Tyr-Pro-Tyr-Phe-Ile-DLys-Leu- (SEQ ID NO: 89),
  xx. Tyr-Pro-Tyr-Phe-Ile-Pro-DLys- (SEQ ID NO: 90),
  xxi. Lys,
  xxii. DLys,
  xxiii. Tyr-Pro-Tyr-Phe-Lys-Pro-Ala- (SEQ ID NO: 91),
  xxiv. Thr-Phe-Lys-Pro-Ala-Asn-Gly- (SEQ ID NO: 92),
  xxv. Gly-Ala-Arg-Phe-Ile-Pro-Ala- (SEQ ID NO: 93),
  xxvi. Tyr-Pro-Lys-Phe-Ile-Pro-Ala- (SEQ ID NO: 94), and
  xxvii. Tyr-Pro-Lys-Phe-Ile-Ser-Ala- (SEQ ID NO: 95).

A certain embodiment of the invention relates to a dual-site BACE1 inhibitor as described herein, wherein B' is selected from the group consisting of
  i. Glu-Val-Asn-Sta-Val-Ala-Glu-DPro-Lys(Chol)-NH$_2$ (SEQ ID NO: 96),
  ii. Glu-Val-Asn-Sta-Asp-Ala-Glu-DPro-Lys(Chol)-NH$_2$ (SEQ ID NO: 97),
  iii. Glu-Val-Asn-Sta-Val-Ala-Glu-DPro-Lys($C^{12}$)—NH$_2$ (SEQ ID NO: 98), iv. Glu-Val-Asn-Sta-Val-Ala-Glu-DPro-Lys(C⁴)—NH₂ (SEQ ID NO: 99),
v. Glu-Val-Asn-Sta-Val-Ala-Glu-DPro-Lys(27-OH-Chol)-NH₂ (SEQ ID NO: 100),
vi. Glu-Val-Asn-Sta-Val-Ala-Glu-DPro-Lys(Chol-27-TFA-ester)-NH₂ (SEQ ID NO: 101),
vii. Glu-Val-Asn-Sta-Val-Ala-Glu-DPro-Lys(Chol'ester')-NH₂ (SEQ ID NO: 102),
viii. Glu-Val-Asn-Sta-Val-Ala-Glu-Phe-Lys(Chol)-NH₂ (SEQ ID NO: 103),
ix. Glu-Val-Asn-MetSta-Val-Ala-Glu-DPhe-Lys(Chol)-NH₂ (SEQ ID NO: 104),
x. Glu-Val-Asn-MetSta-Val-Ala-Glu-DPhe-Lys(C¹⁴)—NH₂ (SEQ ID NO: 105),
xi. Glu-Val-Asn-Leu*Ala-Ala-Glu-DPro-Lys(Chol)-NH₂ (SEQ ID NO: 106),
xii. Glu-Val-Asn-Sta-Val-Ala-Glu-DPro-Lys(Chol'ether')-NH₂ (SEQ ID NO: 107),
xiii. Leu-Pro-Ile-Phe-Tyr-Pro-Tyr-Glu-Val-Asn-Sta-Val-Ala-Glu-DPro-Lys(Chol'ester')-NH₂ (SEQ ID NO: 108),
xiv. Glu-Val-Asn-MetSta-Val-Ala-Glu-Pro-Lys(Chol'ester')-NH₂ (SEQ ID NO: 109), and
xv. Glu-Val-Asn-Leu*Ala-Ala-Glu-DPro-Lys(Chol'ester')-NH₂ (SEQ ID NO: 110).

A certain embodiment of the invention relates to a compound as described herein, selected from the group consisting of Ac-Tyr-Pro-Tyr-Phe-Ile-Pro-Leu-Gly-Gly-Gly-Glu-Val-Asn-Sta-Val-Ala-Glu-DPro-Lys(Chol)-NH₂ (SEQ ID NO: 3),
Ac-Tyr-Pro-Tyr-Phe-Ile-Pro-Leu-PEG(4)-Glu-Val-Asn-Sta-Val-Ala-Glu-DPro-Lys(Chol)-NH₂ (SEQ ID NOS 15 and 96).
DLys-Pro-Tyr-Phe-Ile-Pro-Leu-Gly-DLys-Gly-Glu-Val-Asn-Sta-Val-Ala-Glu-DPro-Lys(Chol'ester')-NH₂ (SEQ ID NO: 55),
DLys(-Gly-DLys-Gly-Leu-Pro-Ile-Phe-Tyr-Pro-Tyr)-Glu-Val-Asn-Sta-Val-Ala-Glu-DPro-Lys(Chol'ester')-NH-2 (SEQ ID NO: 63),
Gly-Ala-Arg-Phe-Ile-Pro-Ala-Gly-DLys-Gly-Glu-Val-Asn-Sta-Val-Ala-Glu-DPro-Lys(Chol'ester')-NH₂ (SEQ ID NO: 68),
Leu-Ile-Tyr-Phe-Pro-Tyr-Pro-Gly-Gly-Gly-Glu-Val-Asn-Sta-Vla-Ala-Glu-DPro-Lys(Chol)-NH₂ (SEQ ID NO: 16),
Leu-Ile-Tyr-Phe-Pro-Tyr-Pro-Gly-Gly-Gly-Glu-Val-Asn-Sta-Val-Ala-Glu-DPro-Lys(Chol)-NH₂ (SEQ ID NO: 17),
Lys-Pro-Tyr-Phe-Ile-Po-Leu-Gly-DLys-Gly-Glu-Val-Asn-Sta-Val-Ala-Glu-DPro-Lys(Chol'ester')-NH₂ (SEQ ID NO: 48),
Lys(-Gly-DLys-Gly-Leu-Pro-Ile-Phe-Tyr-Pro-Tyr)-Glu-Val-Asn-Sta-Val-Ala-Glu-DPro-Lys(Chol'ester')-NH₂ (SEQ ID NO: 62),
Thr-Phe-Lys-Pro-Ala-Asn-Gly-Gly-DLys-Gly-Glu-Val-Asn-Sta-Val-Ala-Glu-DPro-Lys(Chol'ester')-NH₂ (SEQ ID NO: 67),
Tyr-Pro-Tyr-Phe-Ile-Pro-Leu-Gly-Gly-Glu-Val-Asn-Sta-Val-Ala-Glu-DPro-Lys(Cho)-NH₂ (SEQ ID NO: 1),
Tyr-Pro-Tyr-Phe-Ile-Pro-Leu-Gly-Gly-Gly-Glu-Val-Asn-Sta-Val-Ala-Glu-DPro-Lys(Chol)NH₂ (SEQ ID NO: 2),
Tyr-Pro-Tyr-Phe-Ile-Pro-Lu-Gly-Gly-Gly-Glu-Val-Asn-Sta-Asp-Ala-Glu-DPro-Lys(Chol)-NH₂ (SEQ ID NO: 4),
Tyr-Pro-Tyr-Phe-Ile-Pro-Leu-Gly-Gly-Gly-Gly-Glu-Val-Asn-Sta-Val-Ala-Glu-DPro-Lys(Cho)-NH₂ (SEQ ID NO: 5),
Tyr-Pro-Tyr-Phe-Ile-Pro-Leu-Gly-Gly-Gly-Gly-Glu-Val-Asn-Sta-Asp-Ala-Glu-DPro-Lys(Chol)-NH₂ (SEQ ID NO: 6),
Tyr-Pro-Tyr-Phe-Ile-Pro-Leu-Gly-Gly-Gly-Gly-Gly-Ghi-Val-Asn-Sta-Val-Ala-Glu-DPro-Lys(Chol)-NH₂ (SEQ ID NO: 7),
Tyr-Pro-Tyr-Phe-Ile-Pro-Leu-Gly-Gly-Gly-Gly-Gly-Gly-Glu-Val-Asn-Sta-Val-Ala-Glu-DPro-Lys(Chol)-NH₂ (SEQ ID NO: 12),
Tyr-Pro-Tyr-Phe-Ile-Pro-Leu-PEG(3)-Glu-Val-Asn-Sta-Val-Ala-Glu-DPro-Lys(Cho)-NH₂ (SEQ ID NOS 13 and 96),
Tyr-Pro-Tyr-Phe-Ile-Pro-Leu-PEG(4)-Glu-Val-Asn-Sta-Val-Ala-Glu-DPro-Lys(Cho)-NH₂ (SEQ ID NOS 14 and 96),
Tyr-Pro-Tyr-Phe-Ile-Pro-Leu-Gly-Gly-Gly-Glu-Val-Asn-Sta-Val-Ala-Glu-DPro-Lys(C12)-NH₂ (SEQ ID NO: 18),
Tyr-Pro-Tyr-Phe-Ile-Pro-Leu-Gly-Gly-Gly-Glu-Val-Asn-Sta-Val-Ala-Glu-DPro-Lys(C14)-NH₂ (SEQ ID NO: 19),
Tyr-Pro-Tyr-Phe-Ile-Pro-Leu-Gly-Gly-Gly-Glu-Val-Asn-Sta-Val-Ala-Glu-DPro-Lys(27-OH-Chol)-NH₂ (SEQ ID NO: 20),
Tyr-Pro-Tyr-Phe-Ile-Pro-Leu-Gly-Gly-Gly-Glu-Val-Asn-Sta-Val-Ala-Glu-DPro-Lys(Chol-27-TFA-ester)-NH₂ (SEQ ID NO: 21),
Tyr-Pro-Tyr-Phe-Ile-Pro-Leu-Gly-DLys-Gly-Glu-Val-Asn-Sta-Val-Ala-Glu-DPro-Lys(Chol'ester')-NH₂ (SEQ ID NO: 22),
Tyr-Pro-Tyr-Phe-Ile-Pro-Leu-NH(CH2)2CO-Glu-Val-Asn-Sta-Val-Ala-Glu-DPro-Lys(Chol)-NH₂ (SEQ ID NOS 8 and 96),
Tyr-Pro-Tyr-Phe-Ile-Pro-Leu-NH(CH2)4CO-Glu-Val-Asn-Sta-Val-Ala-Glu-DPro-Lys(Chol)-NH₂ (SEQ ID NOS 9 and 96),
Tyr-Pro-Tyr-Phe-Ile-Pro-Leu-NH(CH2)5CO-Glu-Val-Asn-Sta-Val-Ala-Glu-DPro-Lys(Chol)-NH₂ (SEQ ID NOS 10 and 96),
Tyr-Pro-Tyr-Phe-Ile-Pro-Leu-NH(CH2)10CO-Glu-Val-Asn-Sta-Val-Ala-Glu-DPro-Lys(Chol)-NH₂ (SEQ ID NOS 11 and 96),
Tyr-Pro-Tyr-Phe-Ile-Pro-Leu-Gly-Gly-Gly-Glu-Val-Asn-Sta-Val-Ala-Glu-Phe-Lys(Chol)-NH₂ (SEQ ID NO: 23),
Tyr-Pro-Tyr-Phe-Ile-Pro-Leu-Gly-Gly-Gly-Gly-Glu-Val-Asn-MetSta-Val-Ala-Glu-DPhe-Lys(Chol)-NH₂ (SEQ ID NO: 24),
Tyr-Pro-Tyr-Phe-Ile-Pro-Leu-Gly-Gly-Gly-Gly-Gly-Glu-Val-Asn-MetSta-Val-Ala-Glu-DPhe-Lys(Chol)-NH₂ (SEQ ID NO: 25),
Tyr-Pro-Tyr-Phe-Ile-Pro-Leu-PEG(3)-Glu-Val-Asn-MetSta-Val-Ala-Glu-DPhe-Lys(Chol)-NH₂ (SEQ ID NOS 26 and 104),
Tyr-Pro-Tyr-Phe-Ile-Pro-Leu-PEG(4)-Glu-Val-Asn-MetSta-Val-Ala-Glu-DPhe-Lys(Chol)-NH₂ (SEQ ID NOS 27 and 104),
Tyr-Pro-Tyr-Phe-Ile-Pro-Leu-Gly-Gly-Gly-Glu-Val-Asn-MetSta-Val-Ala-Glu-DPh-Lys(C14)-NH₂ (SEQ ID NO: 28),
Tyr-Pro-Tyr-Phe-Ile-Pro-Leu-Gly-Gly-Gly-Glu-Val-Asn-Leu*Ala-Ala-Glu-DPro-Lys(Chol)-NH₂ (SEQ ID NO: 29),
Tyr-Pro-Tyr-Phe-Ile-Pro-Leu-Gly-Gly-Gly-Glu-Val-Asn-Sta-Val-Ala-Glu-DPro-Lys(Chol'ether')-NH₂ (SEQ ID NO: 30),
Tyr-DLys-Tyr-Phe-Ile-Pro-Leu-Gly-DLys-Gly-Glu-Val-Asn-Sta-Val-Ala-Glu-DPro-Lys(Chol'ester')-NH₂ (SEQ ID NO: 56), Tyr-Lys-Tyr-Phe-Ile-Pro-Lcu-Gly-DLys-Gly-Glu-Val-Asn-Sta-Val-Ala-Glu-DPro-Lys(Chol'ester')-NH$_2$ (SEQ ID NO: 49),
Tyr-Pro-DLys-Phe-Ile-Pro-Leu-Gly-DLys-Gly-Glu-Val-Asn-Sta-Val-Ala-Glu-DPro-Lys(Chol'ester')-NH$_2$ (SEQ ID NO: 57),
Tyr-Pro-Lys-Phe-Ile-Lys-Leu-Gly-DLys-Gly-Glu-Val-Asn-Sta-Val-Ala-lu-DPro-Lys(Chol)-NH$_2$ (SEQ ID NO: 46),
Tyr-Pro-Lys-Phe-Ile-Pro-Ala-Gly-DLys-Gly-Glu-Val-Asn-Sta-Vai-Ala-Glu-DPro-Lys(Chol'ester')-NH$_2$ (SEQ ID NO: 69),
Tyr-Pro-Lys-Phe-Ile-Pro-Leu-Gly-DLys-Gly-Glu-Val-Asn-Leu*Ala-Ala-Glu-DPro-Lys(Chol'ester')-NH$_2$ (SEQ ID NO: 65),
Tyr-Pro-Lys-Phe-Ile-Pro-Leu-Gly-DLys-Gly-Glu-Val-Asn-MetSta-Val-Ala-Glu-Pro-Lys(Chol'ester')-NH$_2$ (SEQ ID NO: 64),
Tyr-Pro-Lys-Phe-Ile-Po-Leu-Gly-DLys-Gly-Glu-Val-Asn-Sta-Val-Ala-Glu-DPro-Lys(Chol)-NH$_2$ (SEQ ID NO: 36),
Tyr-Pro-Lys-Phe-Ile-Pro-Leu-Gly-DLys-Gly-Glu-Val-Asn-Sta-Val-Ala-Glu-DPro-Lys(Chol'ether')-NH$_2$ (SEQ ID NO: 44),
Tyr-Pro-Lys-Phc-Ile-Pro-Leu-Gly-Gly-Gly-Glu-Val-Asn-Sta-Val-Ala-Glu-DPro-Lys(Cho)-NH$_2$ (SEQ ID NO: 31),
Tyr-Pro-Lys-Phe-Ile-Ser-Ala-Gly-DLys-Gly-Glu-Val-Asn-Sta-Val-Ala-Glu-DPro-Lys(Chol'ester')-NH$_2$ (SEQ ID NO: 70),
Tyr-Pro-Lys-Phe-Lys-Lys-Leu-Gly-DLys-Gly-Glu-Val-Asn-Sta-Val-Ala-Glu-DPro-Lys(Chol)-NH$_2$ (SEQ ID NO: 47),
Tyr-Pro-Lys-Phe-Lys-Pro-Leu-Gly-DLys-Gly-Glu-Val-Asn-Sta-Val-Ala-Glu-DPro-Lys(Chol)-NH$_2$ (SEQ ID NO: 45),
Tyr-Pro-Tyr-DLys-Ile-Pro-Leu-Gly-DLys-Gly-Glu-Val-Asn-Sta-Val-Ala-Glu-DPro-Lys(Chol'ester')-NH$_2$ (SEQ ID NO: 58),
Tyr-Pro-Tyr-Lys-Ile-Pro-Leu-Gly-DLys-Gly-Glu-Val-Asn-Sta-Val-Ala-Glu-DPro-Lys(Chol'ester')-NH$_2$ (SEQ ID NO: 50),
Tyr-Pro-Tyr-Phe-DLys-Pro-Leu-Gly-DLys-Gly-Glu-Val-Asn-Sta-Val-Ala-Glu-DPro-Lys(Chol'ester')-NH$_2$ (SEQ ID NO: 59),
Tyr-Pro-Tyr-Phe-Ile-DLys-Leu-Gly-DLys-Gly-Glu-Val-Asn-Sta-Val-Ala-Glu-DPro-Lys(Chol'ester')-NH$_2$ (SEQ ID NO: 60),
Tyr-Pro-Tyr-Phe-Ile-Lys-Lu-Gly-DLys-Gly-Glu-Val-Asn-Sta-Val-Ala-Glu-DPro-Lys(Chol)-NH$_2$ (SEQ ID NO: 38),
Tyr-Pro-Tyr-Phe-Ile-Lys-Leu-Gly-Gly-Gly-Glu-Val-Asn-Sta-Val-Ala-Glu-DPro-Lys(Chol)-NH$_2$ (SEQ ID NO: 33),
Tyr-Pro-Tyr-Phe-Ile-Lys-Leu-PEG(4)-Glu-Val-Asn-Sta-Val-Ala-Glu-DPro-Lys(Chol)-NH$_2$ (SEQ ID NOS 35 and 96),
Tyr-Pr-Tyr-Phe-Ile-Pro-DLys-Gly-DLys-Gly-Glu-Val-Asn-Sta-Val-Ala-Glu-DPro-Lys(Chol'ester')-NH$_2$ (SEQ ID NO: 61),
Tyr-Pro-Tyr-Phe-Ile-Pro-Leu-DAla-Gly-Gly-Glu-Val-Asn-Sta-Val-Ala-Glu-DPro-Lys(Chol'ester')-NH$_2$ (SEQ ID NO: 52),
Tyr-Pro-Tyr-Phe-Ile-Pro-Leu-DLys-Gly-Gly-Glu-Val-Asn-Sta-Val-Ala-Glu-DPro-Lys(Chol)-NH$_2$ (SEQ ID NO: 41),
Tyr-Pro-Tyr-Phe-Ile-Pro-Leu-Gly-DAla-Gly-Glu-Val-Asn-Sta-Val-Ala-Glu-DPro-Lys(Chol'ester')-NH$_2$ (SEQ ID NO: 53),
Tyr-Pro-Tyr-Phe-Ile-Pro-Leu-Gly-Gly-DLys-Glu-Val-Asn-Sa-Val-Ala-Glu-DPro-Lys(Chol)-NH$_2$ (SEQ ID NO: 43),
Tyr-Pro-Tyr-Phe-Ile-Pro-Leu-Gly-Gly-Lys-Glu-Val-Asn-Sta-Val-Ala-Glu-DPro-Lys(Chol)-NH$_2$ (SEQ ID NO: 42),
Tyr-Pro-Tyr-Phe-Ile-Pro-Leu-Gly-Lys-Gly-Glu-Val-Asn-Sta-Val-Ala-Glu-DPro-Lys(Chol)-NH$_2$ (SEQ ID NO: 39),
Tyr-Pro-Tyr-Phe-Ile-Pro-Leu-Lys-Gly-Gly-Glu-Val-Asn-Sta-Val-Ala-Glu-DPro-Lys(Chol)-NH$_2$ (SEQ ID NO: 40),
Tyr-Pro-Tyr-Phe-Ile-Pro-Leu-Ser-Gly-Gly-Glu-Val-Asn-Sta-Val-Ala-Glu-DPro-Lys(Chol'ester')-NH$_2$ (SEQ ID NO: 54),
Tyr-Pro-Tyr-Phe-Ile-Pro-Lys-Gly-DLys-Gly-Glu-Val-Asn-Sta-Val-Ala-Glu-DPro-Lys(Chol'ester')-NH$_2$ (SEQ ID NO: 51),
Tyr-Pro-Tyr-Phe-Lys-Pro-Ala-Gly-DLys-Gly-Glu-Val-Asn-Sta-Val-Ala-Glu-DPro-Lys(Chol'ester')-NH$_2$ (SEQ ID NO: 66),
Tyr-Pro-Tyr-Phe-Lys-Pro-Leu-Gly-DLys-Gly-lu-Val-Asn-Sta-Val-Ala-Glu-DPro-Lys(Cho)-NH$_2$ (SEQ ID NO: 37),
Tyr-Pro-Tyr-Phe-Lys-Pro-Leu-Gly-Gly-Gly-Glu-Val-Asn-Sta-Val-Ala-Glu-DPro-Lys(Cho)-NH$_2$ (SEQ ID NO: 32), and
Tyr-Pro-Tyr-Phe-Lys-Pro-Leu-PEG(4)-Glu-Val-Asn-Sta-Val-Ala-Glu-DPro-Lys(Chol)-NH$_2$ (SEQ ID NOS 34 and 96),
or a pharmaceutical acceptable salt thereof.

A certain embodiment of the invention relates to a compound as described herein, wherein the pharmaceutically acceptable salt is trifluoroacetate.

A certain embodiment of the invention relates to a dual-site BACE1 inhibitor as described herein for use as therapeutically active substance.

A certain embodiment of the invention relates to a dual-site BACE1 inhibitor as described herein for the use as inhibitor of BACE1 activity.

A certain embodiment of the invention relates to a dual-site BACE1 inhibitor as described herein for the use as therapeutically active substance for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention relates to a dual-site BACE1 inhibitor as described herein for the use as therapeutically active substance for the therapeutic and/or prophylactic treatment of Alzheimer's disease.

A certain embodiment of the invention relates to a pharmaceutical composition comprising a dual-site BACE1 inhibitor as described herein and a pharmaceutically acceptable carrier and/or a pharmaceutically acceptable auxiliary substance.

A certain embodiment of the invention relates to the use of a dual-site BACE1 inhibitor as described herein for the manufacture of a medicament for the use in inhibition of BACE1 activity.

A certain embodiment of the invention relates to a dual-site BACE inhibitor as described herein for the manufacture of a medicament for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention relates to the use of a dual-site BACE1 inhibitor as described herein for the manufacture of a medicament for the therapeutic and/or prophylactic treatment of Alzheimer's disease.

A certain embodiment of the invention relates to a dual-site BACE1 inhibitor as described herein for the use in inhibition of BACE1 activity.

A certain embodiment of the invention relates to a dual-site BACE1 inhibitor as described herein for the use in the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention relates to a dual-site BACE1 inhibitor as described herein for the use in the therapeutic and/or prophylactic treatment of Alzheimer's disease.

A certain embodiment of the invention relates to a method for the use in inhibition of BACE1 activity, particularly for the therapeutic and/or prophylactic treatment of diseases and disorders characterized by elevated β-amyloid levels and/or β-amyloid oligomers and/or β-amyloid plaques and further deposits, Alzheimer's disease, which method comprises administering dual-site BACE1 inhibitor as described herein to a human being or animal.

Furthermore, the invention includes all optical isomers, i.e. diastereoisomers, diastereomeric mixtures, racemic mixtures, all their corresponding enantiomers and/or tautomers as well as their solvates.

The dual-site BACE1 inhibitors may be prepared as described herein. The starting material is commercially available or may be prepared in accordance with known methods.

The corresponding pharmaceutically acceptable salts with acids can be obtained by standard methods known to the person skilled in the art, e.g. by dissolving the dual-site BACE1 inhibitor in a suitable solvent such as e.g. dioxan or THF and adding an appropriate amount of the corresponding acid. The products can usually be isolated by filtration or by chromatography. The conversion of a dual-site BACE1 inhibitor into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the dual-site BACE1 inhibitors as well as all intermediate products can be prepared according to analogous methods or according to the methods set forth herewithin. Starting materials are commercially available, known in the art or can be prepared by methods known in the art or in analogy thereto.

It will be appreciated that the dual-site BACE1 inhibitors in this invention may be derivatised at functional groups to provide derivatives which are capable of conversion back to the parent compound in vivo.

Pharmacological Tests

The dual-site BACE1 inhibitor and their pharmaceutically acceptable salts possess valuable pharmacological properties. It has been found that the compounds of the present invention are associated with inhibition of BACE1 activity. The compounds were investigated in accordance with the test given hereinafter.

Cellular Aβ-Lowering Assay:

Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96 well ELISA plates (e.g., Nunc MaxiSorb) were coated with monoclonal antibody which specifically recognize the C-terminal end of Aβ40 (Brockhaus et al., NeuroReport 9; 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/$H_2O_2$ in citric acid buffer. After stopping the reaction with one volume 1 N $H_2SO_4$ the reaction was measured in an ELISA reader at 450 nm wavelength. The concentrations of Aβ in the culture supernatants were calculated from a standard curve obtained with known amounts of pure Aβ peptide.

TABLE 2

IC50 values of selected examples

| Ex. | SEQ ID NO: | Name | Systematic Name | MW | IC 50 (μM) |
|---|---|---|---|---|---|
| 1 | 1 | YPYFIPLGG-EVN-Sta-VAE-DPro-K(Chol)-NH₂ x TFA | Tyr-Pro-Tyr-Phe-Ile-Pro-Leu-Gly-Gly-Glu-Val-Asn-Sta-Val-Ala-Glu-DPro-Lys(Chol)-NH₂ x TFA | 2632.1 | 0.00027 |
| 2 | 2 | YPYFIPLGGG-EVN-Sta-VAE-DPro-K(Chol)-NH₂ x TFA | Tyr-Pro-Tyr-Phe-Ile-Pro-Leu-Gly-Gly-Gly-Glu-Val-Asn-Sta-Val-Ala-Glu-DPro-Lys(Chol)-NH₂ x TFA | 2689.2 | 0.000027 |
| 3 | 2 | Ac-YPYFIPLGGG-EVN-Sta-VAE-DPro-K(Chol)-NH₂ x TFA | Ac-Tyr-Pro-Tyr-Phe-Ile-Pro-Leu-Gly-Gly-Gly-Glu-Val-Asn-Sta-Val-Ala-Glu-DPro-Lys(Chol)-NH₂ | 2617.2 | 0.000017 |
| 4 | 4 | YPYFIPL-GGG-EVN-Sta-DAE-DPro-K(Chol)-NH₂ x TFA | Tyr-Pro-Tyr-Phe-Ile-Pro-Leu-Gly-Gly-Gly-Glu-Val-Asn-Sta-Asp-Ala-Glu-DPro-Lys(Chol)-NH₂ x TFA | 2705.1 | 0.018 |

TABLE 2-continued

IC50 values of selected examples

| Ex. | SEQ ID NO: | Name | Systematic Name | MW | IC 50 (µM) |
|---|---|---|---|---|---|
| 5 | 5 | YPYFIPLGGGG-EVN-Sta-VAE-DPro-K(Chol)-NH₂ x TFA | Tyr-Pro-Tyr-Phe-Ile-Pro-Leu-Gly-Gly-Gly-Gly-Glu-Val-Asn-Sta-Val-Ala-Glu-DPro-Lys(Chol)-NH₂ x TFA | 2746.2 | 0.000042 |
| 6 | 6 | YPYFIPL-GGGG-EVN-Sta-DAE-DPro-K(Chol)-NH₂ x TFA | Tyr-Pro-Tyr-Phe-Ile-Pro-Leu-Gly-Gly-Gly-Gly-Glu-Val-Asn-Sta-Asp-Ala-Glu-DPro-Lys(Chol)-NH₂ x TFA | 2762.2 | 0.0033 |
| 7 | 7 | YPYFIPLGGGGG-EVN-Sta-VAE-DPro-K(Chol)-NH₂ x TFA | Tyr-Pro-Tyr-Phe-Ile-Pro-Leu-Gly-Gly-Gly-Gly-Gly-Glu-Val-Asn-Sta-Val-Ala-Glu-DPro-Lys(Chol)-NH₂ x TFA | 2803.3 | 0.000044 |
| 8 | 8 and 96 | YPYFIPL-NH(CH2)2CO-EVN-Sta-VAE-DPro-K(Chol)-NH₂ x TFA | Tyr-Pro-Tyr-Phe-Ile-Pro-Leu-NH(CH2)2CO-Glu-Val-Asn-Sta-Val-Ala-Glu-DPro-Lys(Chol)-NH₂ x TFA | 2589.1 | 0.0028 |
| 9 | 9 and 96 | YPYFIPL-NH(CH2)4CO-EVN-Sta-VAE-DPro-K(Chol)-NH₂ x TFA | Tyr-Pro-Tyr-Phe-Ile-Pro-Leu-NH(CH2)4CO-Glu-Val-Asn-Sta-Val-Ala-Glu-DPro-Lys(Chol)-NH₂ x TFA | 2617.1 | 0.00084 |
| 10 | 10 and 96 | YPYFIPL-NH(CH2)5CO-EVN-Sta-VAE-DPro-K(Chol)-NH₂ x TFA | Tyr-Pro-Tyr-Phe-Ile-Pro-Leu-NH(CH2)5CO-Glu-Val-Asn-Sta-Val-Ala-Glu-DPro-Lys(Chol)-NH₂ x TFA | 2631.2 | 0.000075 |
| 11 | 11 and 96 | YPYFIPL-NH(CH2)10CO-EVN-Sta-VAE-DPro-K(Chol)-NH₂ x TFA | Tyr-Pro-Tyr-Phe-Ile-Pro-Leu-NH(CH2)10CO-Glu-Val-Asn-Sta-Val-Ala-Glu-DPro-Lys(Chol)-NH₂ x TFA | 2701.3 | 0.00036 |
| 12 | 12 | YPYFIPLGGGGGG-EVN-Sta-VAE-DPro-K(Chol)-NH₂ x TFA | Tyr-Pro-Tyr-Phe-Ile-Pro-Leu-Gly-Gly-Gly-Gly-Gly-Gly-Glu-Val-Asn-Sta-Val-Ala-Glu-DPro-Lys(Chol)-NH₂ x TFA | 2860.3 | 0.000028 |
| 13 | 13 and 96 | YPYFIPL-PEG(3)-EVN-Sta-VAE-DPro-K(Chol)-NH₂ x TFA | Tyr-Pro-Tyr-Phe-Ile-Pro-Leu-PEG(3)-Glu-Val-Asn-Sta-Val-Ala-Glu-DPro-Lys(Chol)-NH₂ x TFA | 2721.2 | 0.000043 |
| 14 | 14 and 96 | YPYFIPL-PEG(4)-EVN-Sta-VAE-DPro-K(Chol)-NH₂ x TFA | Tyr-Pro-Tyr-Phe-Ile-Pro-Leu-PEG(4)-Glu-Val-Asn-Sta-Val-Ala-Glu-DPro-Lys(Chol)-NH₂ x TFA | 2765.3 | 0.000027 |
| 15 | 15 and 96 | Ac-YPYFIPL-PEG(4)-EVN-Sta-VAE-DPro-K(Chol)-NH₂ | Ac-Tyr-Pro-Tyr-Phe-Ile-Pro-Leu-PEG(4)-Glu-Val-Asn-Sta-Val-Ala-Glu-DPro-Lys(Chol)-NH₂ | 2693.3 | 0.000041 |
| 16 | 16 | LIYFPYP-GGG-EVN-Sta-VAE-DPro-K(Chol)-NH₂ x TFA | Leu-Ile-Tyr-Phe-Pro-Tyr-Pro-Gly-Gly-Gly-Glu-Val-Asn-Sta-Val-Ala-Glu-DPro-Lys(Chol)-NH₂ x TFA | 2689.2 | 0.00022 |
| 17 | 17 | LIYFPYP-GGGG-EVN-Sta-VAE-DPro-K(Chol)-NH₂ x TFA | Leu-Ile-Tyr-Phe-Pro-Tyr-Pro-Gly-Gly-Gly-Gly-Glu-Val-Asn-Sta-Val-Ala-Glu-DPro-Lys(Chol)-NH₂ x TFA | 2746.2 | 0.00028 |
| 18 | 18 | YPYFIPL-GGG-EVN-Sta-VAE-DPro-K(C12)-NH₂ x TFA | Tyr-Pro-Tyr-Phe-Ile-Pro-Leu-Gly-Gly-Gly-Glu-Val-Asn-Sta-Val-Ala-Glu-DPro-Lys($C^{12}$)-NH₂ x TFA | 2402.7 | 0.45 |
| 19 | 19 | YPYFIPL-GGG-EVN-Sta-VAE-DPro-K(C14)-NH₂ x TFA | Tyr-Pro-Tyr-Phe-Ile-Pro-Leu-Gly-Gly-Gly-Glu-Val-Asn-Sta-Val-Ala-Glu-DPro-Lys($C^{14}$)-NH₂ x TFA | 2430.8 | 0.14 |
| 20 | 20 | YPYFIPL-GGG-EVN-Sta-VAE-DPro-K(27-OH-Chol)-NH₂ x TFA | Tyr-Pro-Tyr-Phe-Ile-Pro-Leu-Gly-Gly-Gly-Glu-Val-Asn-Sta-Val-Ala-Glu-DPro-Lys(27-OH-Chol)-NH₂ x TFA | 2705.2 | 0.0063 |

TABLE 2-continued

IC50 values of selected examples

| Ex. | SEQ ID NO: | Name | Systematic Name | MW | IC 50 (µM) |
|---|---|---|---|---|---|
| 21 | 21 | YPYFIPL-GGG-EVN-Sta-VAE-DPro-K(Chol-27-TFA-ester)-NH$_2$ x TFA | Tyr-Pro-Tyr-Phe-Ile-Pro-Leu-Gly-Gly-Gly-Glu-Val-Asn-Sta-Val-Ala-Glu-DPro-Lys(Chol-27-TFA-ester)-NH$_2$ x TFA | 2801.2 | 0.0052 |
| 22 | 22 | YPYFIPL-GkG-EVN-Sta-VAE-DPro-K(Chol'estert)-NH$_2$ x 2TFA | Tyr-Pro-Tyr-Phe-Ile-Pro-Leu-Gly-DLys-Gly-Glu-Val-Asn-Sta-Val-Ala-Glu-DPro-Lys(Chol'estert)-NH$_2$ x 2TFA | 2874.3 | 0.000025 |
| 23 | 23 | YPYFIPLGGGEVN-Sta-VAEFK(Chol)-NH$_2$ x TFA | Tyr-Pro-Tyr-Phe-Ile-Pro-Leu-Gly-Gly-Gly-Glu-Val-Asn-Sta-Val-Ala-Glu-Phe-Lys(Chol)-NH$_2$ x TFA | 2739.2 | 0.00019 |
| 24 | 24 | YPYFIPL-GGGG-EVN-MetSta-VAE-DPhe-K(Chol)-NH$_2$ x TFA | Tyr-Pro-Tyr-Phe-Ile-Pro-Leu-Gly-Gly-Gly-Gly-Glu-Val-Asn-MetSta-Val-Ala-Glu-DPhe-Lys(Chol)-NH$_2$ x TFA | 2814.3 | 0.000052 |
| 25 | 25 | YPYFIPL-GGGGG-EVN-MetSta-VAE-DPhe-K(Chol)-NH$_2$ x TFA | Tyr-Pro-Tyr-Phe-Ile-Pro-Leu-Gly-Gly-Gly-Gly-Gly-Glu-Val-Asn-MetSta-Val-Ala-Glu-DPhe-Lys(Chol)-NH$_2$ x TFA | 2871.4 | 0.000070 |
| 26 | 26 and 104 | YPYFIPL-PEG(3)-EVN-MetSta-VAE-DPhe-K(Chol)-NH$_2$ x TFA | Tyr-Pro-Tyr-Phe-Ile-Pro-Leu-PEG(3)-Glu-Val-Asn-MetSta-Val-Ala-Glu-DPhe-Lys(Chol)-NH$_2$ x TFA | 2789.3 | 0.000036 |
| 27 | 27 and 104 | YPYFIPL-PEG(4)-EVN-MetSta-VAE-DPhe-K(Chol)-NH$_2$ x TFA | Tyr-Pro-Tyr-Phe-Ile-Pro-Leu-PEG(4)-Glu-Val-Asn-MetSta-Val-Ala-Glu-DPhe-Lys(Chol)-NH$_2$ x TFA | 2833.4 | 0.000018 |
| 28 | 28 | YPYFIPL-GGG-EVN-MetSta-VAE-DPhe-K(C14)-NH$_2$ x TFA | Tyr-Pro-Tyr-Phe-Ile-Pro-Leu-Gly-Gly-Gly-Glu-Val-Asn-MetSta-Val-Ala-Glu-DPhe-Lys(C14)-NH$_2$ x TFA | 2498.9 | 1.26 |
| 29 | 29 | YPYFIPLGGGEVN-Leu*Ala-AE-DPro-K(Chol)-NH$_2$ x TFA | Tyr-Pro-Tyr-Phe-Ile-Pro-Leu-Gly-Gly-Gly-Glu-Val-Asn-Leu*Ala-Ala-Glu-DPro-Lys(Chol)-NH$_2$ x TFA | 2618.1 | 0.0000024 |
| 30 | 30 | YPYFIPL-GGG-EVN-Sta-VAE-DPro-K(Chorethert)-NH$_2$ x TFA | Tyr-Pro-Tyr-Phe-Ile-Pro-Leu-Gly-Gly-Gly-Glu-Val-Asn-Sta-Val-Ala-Glu-DPro-Lys(Chorethert)-NH$_2$ x TFA | 2746.3 | 0.0000264 |
| 31 | 31 | YPKFIPL-GGG-EVN-Sta-VAE-DPro-K(Chol)-NH$_2$ x 2TFA | Tyr-Pro-Lys-Phe-Ile-Pro-Leu-Gly-Gly-Gly-Glu-Val-Asn-Sta-Val-Ala-Glu-DPro-Lys(Chol)-NH$_2$ x 2TFA | 2768.2 | 0.0000135 |
| 32 | 32 | YPYFKPL-GGG-EVN-Sta-VAE-DPro-K(Chol)-NH$_2$ | Tyr-Pro-Tyr-Phe-Lys-Pro-Leu-Gly-Gly-Gly-Glu-Val-Asn-Sta-Val-Ala-Glu-DPro-Lys(Chol)-NH$_2$ x 2TFA | 2818.2 | 0.00000732 |
| 33 | 33 | YPYFIKL-GGG-EVN-Sta-VAE-DPro-K(Chol)-NH$_2$ x 2TFA | Tyr-Pro-Tyr-Phe-Ile-Lys-Leu-Gly-Gly-Gly-Glu-Val-Asn-Sta-Val-Ala-Glu-DPro-Lys(Chol)-NH$_2$ x 2TFA | 2834.2 | 0.0000117 |
| 34 | 34 and 96 | YPYFKPL-PEG(4)-EVN-Sta-VAE-DPro-K(Chol)-NH$_2$ x 2TFA | Tyr-Pro-Tyr-Phe-Lys-Pro-Leu-PEG(4)-Glu-Val-Asn-Sta-Val-Ala-Glu-DPro-Lys(Chol)-NH$_2$ x 2TFA | 2894.3 | 0.0000235 |
| 35 | 35 and 96 | YPYFIKL-PEG(4)-EVN-Sta-VAE-DPro-K(Chol)-NH$_2$ x 2TFA | Tyr-Pro-Tyr-Phe-Ile-Lys-Leu-PEG(4)-Glu-Val-Asn-Sta-Val-Ala-Glu-DPro-Lys(Chol)-NH$_2$ x 2TFA | 2910.4 | 0.0000228 |
| 36 | 36 | YPKFIPL-GkG-EVN-Sta-VAE-DPro-K(Chol)-NH$_2$ x 3TFA | Tyr-Pro-Lys-Phe-Ile-Pro-Leu-Gly-DLys-Gly-Glu-Val-Asn-Sta-Val-Ala-Glu-DPro-Lys(Chol)-NH$_2$ x 3TFA | 2953.3 | 0.0000203 |

TABLE 2-continued

IC50 values of selected examples

| Ex. | SEQ ID NO: | Name | Systematic Name | MW | IC 50 (µM) |
|---|---|---|---|---|---|
| 37 | 37 | YPYFKPL-GkG-EVN-Sta-VAE-DPro-K(Chol)-NH₂ x 3TFA | Tyr-Pro-Tyr-Phe-Lys-Pro-Leu-Gly-DLys-Gly-Glu-Val-Asn-Sta-Val-Ala-Glu-DPro-Lys(Chol)-NH₂ x 3TFA | 3003.3 | 0.0000263 |
| 38 | 38 | YPYFIKL-GkG-EVN-Sta-VAE-DPro-K(Chol)-NH₂ x 3TFA | Tyr-Pro-Tyr-Phe-Ile-Lys-Leu-Gly-DLys-Gly-Glu-Val-Asn-Sta-Val-Ala-Glu-DPro-Lys(Chol)-NH₂ x 3TFA | 3019.4 | 0.0000176 |
| 39 | 39 | YPYFIPL-GkG-EVN-Sta-VAE-DPro-K(Chol)-NH₂ x 2TFA | Tyr-Pro-Tyr-Phe-Ile-Pro-Leu-Gly-Lys-Gly-Glu-Val-Asn-Sta-Val-Ala-Glu-DPro-Lys(Chol)-NH₂ x 2TFA | 2874.3 | 0.0000295 |
| 40 | 40 | YPYFIPL-KGG-EVN-Sta-VAE-DPro-K(Chol)-NH₂ x 2TFA | Tyr-Pro-Tyr-Phe-Ile-Pro-Leu-Lys-Gly-Gly-Glu-Val-Asn-Sta-Val-Ala-Glu-DPro-Lys(Chol)-NH₂ x 2TFA | 2874.3 | 0.0000235 |
| 41 | 41 | YPYFIPL-kGG-EVN-Sta-VAE-DPro-K(Chol)-NH₂ x 2TFA | Tyr-Pro-Tyr-Phe-Ile-Pro-Leu-DLys-Gly-Gly-Glu-Val-Asn-Sta-Val-Ala-Glu-DPro-Lys(Chol)-NH₂ x 2TFA | 2874.3 | 0.000177 |
| 42 | 42 | YPYFIPL-GGK-EVN-Sta-VAE-DPro-K(Chol)-NH₂ x 2TFA | Tyr-Pro-Tyr-Phe-Ile-Pro-Leu-Gly-Gly-Lys-Glu-Val-Asn-Sta-Val-Ala-Glu-DPro-Lys(Chol)-NH₂ x 2TFA | 2874.3 | 0.0000771 |
| 43 | 43 | YPYFIPL-GGk-EVN-Sta-VAE-DPro-K(Chol)-NH₂ x 2TFA | Tyr-Pro-Tyr-Phe-Ile-Pro-Leu-Gly-Gly-DLys-Glu-Val-Asn-Sta-Val-Ala-Glu-DPro-Lys(Chol)-NH₂ x 2TFA | 2874.3 | 0.000118 |
| 44 | 44 | YPKFIPL-GkG-EVN-Sta-VAE-DPro-K(Chorethert)-NH₂ x 3TFA | Tyr-Pro-Lys-Phe-Ile-Pro-Leu-Gly-DLys-Gly-Glu-Val-Asn-Sta-Val-Ala-Glu-DPro-Lys(Chorethert)-NH₂ x 3TFA | 3010.4 | 0.00000828 |
| 45 | 45 | YPKFKPL-GkG-EVN-Sta-VAE-DPro-K(Chol)-NH₂ x 4TFA | Tyr-Pro-Lys-Phe-Lys-Pro-Leu-Gly-DLys-Gly-Glu-Val-Asn-Sta-Val-Ala-Glu-DPro-Lys(Chol)-NH₂ x 4TFA | 3082.4 | 0.0000218 |
| 46 | 46 | YPKFIKL-GkG-EVN-Sta-VAE-DPro-K(Chol)-NH₂ x 4TFA | Tyr-Pro-Lys-Phe-Ile-Lys-Leu-Gly-DLys-Gly-Glu-Val-Asn-Sta-Val-Ala-Glu-DPro-Lys(Chol)-NH₂ x 4TFA | 3098.4 | |
| 47 | 47 | YPKFKKL-GkG-EVN-Sta-VAE-DPro-K(Chol)-NH₂ x 5TFA | Tyr-Pro-Lys-Phe-Lys-Lys-Leu-Gly-DLys-Gly-Glu-Val-Asn-Sta-Val-Ala-Glu-DPro-Lys(Chol)-NH₂ x 5TFA | 3227.4 | |
| 48 | 48 | KPYFIPL-GkG-EVN-Sta-VAEp-K(Chol'estert)-NH₂ x 3TFA | Lys-Pro-Tyr-Phe-Ile-Pro-Leu-Gly-DLys-Gly-Glu-Val-Asn-Sta-Val-Ala-Glu-DPro-Lys(Chol'estert)-NH₂ x 3TFA | 2953.3 | 0.000020 |
| 49 | 49 | YKYFIPL-GkG-EVN-Sta-VAEp-K(Chol'estert)-NH₂ x 3TFA | Tyr-Lys-Tyr-Phe-Ile-Pro-Leu-Gly-DLys-Gly-Glu-Val-Asn-Sta-Val-Ala-Glu-DPro-Lys(Chol'estert)-NH₂ x 3TFA | 3019.4 | 0.00025 |
| 50 | 50 | YPYKIPL-GkG-EVN-Sta-VAEp-K(Chol'estert)-NH₂ x 3TFA | Tyr-Pro-Tyr-Lys-Ile-Pro-Leu-Gly-DLys-Gly-Glu-Val-Asn-Sta-Val-Ala-Glu-DPro-Lys(Chol'estert)-NH₂ x 3TFA | 2969.3 | 0.0023 |
| 51 | 51 | YPYFIPK-GkG-EVN-Sta-VAEp-K(Chol'estert)-NH₂ x 3TFA | Tyr-Pro-Tyr-Phe-Ile-Pro-Lys-Gly-DLys-Gly-Glu-Val-Asn-Sta-Val-Ala-Glu-DPro-Lys(Chol'estert)-NH₂ x 3TFA | 3003.3 | 0.000012 |

TABLE 2-continued

IC50 values of selected examples

| Ex. | SEQ ID NO: | Name | Systematic Name | MW | IC 50 (µM) |
|---|---|---|---|---|---|
| 52 | 52 | YPYFIPL-aGG-EVN-Sta-VAEp-K(Chol'estert)-NH₂ x TFA | Tyr-Pro-Tyr-Phe-Ile-Pro-Leu-DAla-Gly-Gly-Glu-Val-Asn-Sta-Val-Ala-Glu-DPro-Lys(Chol'estert)-NH₂ x TFA | 2703.2 | 0.000055 |
| 53 | 53 | YPYFIPL-GaG-EVN-Sta-VAEp-K(Chol'ester')-NH₂ x TFA | Tyr-Pro-Tyr-Phe-Ile-Pro-Leu-Gly-DAla-Gly-Glu-Val-Asn-Sta-Val-Ala-Glu-DPro-Lys(Chol'ester')-NH₂ x TFA | 2703.2 | 0.000020 |
| 54 | 54 | YPYFIPL-SGG-EVN-Sta-VAEp-K(Chol'ester')-NH₂ x TFA | Tyr-Pro-Tyr-Phe-Ile-Pro-Leu-Ser-Gly-Gly-Glu-Val-Asn-Sta-Val-Ala-Glu-DPro-Lys(Chol'ester')-NH₂ x TFA | 2719.2 | 0.000052 |
| 55 | 55 | kPYFIPL-GkG-EVN-Sta-VAEp-K(Chol'ester')-NH₂ x 3TFA | DLys-Pro-Tyr-Phe-Ile-Pro-Leu-Gly-DLys-Gly-Glu-Val-Asn-Sta-Val-Ala-Glu-DPro-Lys(Chol'ester')-NH₂ x 3TFA | 2953.3 | 0.000013 |
| 56 | 56 | YkYFIPL-GkG-EVN-Sta-VAEp-K(Chol'ester')-NH₂ x 3TFA | Tyr-DLys-Tyr-Phe-Ile-Pro-Leu-Gly-DLys-Gly-Glu-Val-Asn-Sta-Val-Ala-Glu-DPro-Lys(Chol'ester')-NH₂ x 3TFA | 3019.4 | 0.0034 |
| 57 | 57 | YPkFIPL-GkG-EVN-Sta-VAEp-K(Chol'ester')-NH₂ x 3TFA | Tyr-Pro-DLys-Phe-Ile-Pro-Leu-Gly-DLys-Gly-Glu-Val-Asn-Sta-Val-Ala-Glu-DPro-Lys(Chol'ester')-NH₂ x 3TFA | 2953.3 | 0.00078 |
| 58 | 58 | YPYkIPL-GkG-EVN-Sta-VAEp-K(Chol'ester')-NH₂ x 3TFA | Tyr-Pro-Tyr-DLys-Ile-Pro-Leu-Gly-DLys-Gly-Glu-Val-Asn-Sta-Val-Ala-Glu-DPro-Lys(Chol'ester')-NH₂ x 3TFA | 2969.3 | 0.0065 |
| 59 | 59 | YPYFkPL-GkG-EVN-Sta-VAEp-K(Chol'ester')-NH₂ x 3TFA | Tyr-Pro-Tyr-Phe-DLys-Pro-Leu-Gly-DLys-Gly-Glu-Val-Asn-Sta-Val-Ala-Glu-DPro-Lys(Chol'ester')-NH₂ x 3TFA | 3003.3 | 0.0076 |
| 60 | 60 | YPYFIkL-GkG-EVN-Sta-VAEp-K(Chol'ester')-NH₂ x 3TFA | Tyr-Pro-Tyr-Phe-Ile-DLys-Leu-Gly-DLys-Gly-Glu-Val-Asn-Sta-Val-Ala-Glu-DPro-Lys(Chol'ester')-NH₂ x 3TFA | 3019.4 | 0.00045 |
| 61 | 61 | YPYFIPk-GkG-EVN-Sta-VAEp-K(Chol'ester')-NH₂ x 3TFA | Tyr-Pro-Tyr-Phe-Ile-Pro-DLys-Gly-DLys-Gly-Glu-Val-Asn-Sta-Val-Ala-Glu-DPro-Lys(Chol'ester')-NH₂ x 3TFA | 3003.3 | 0.0000059 |
| 62 | 62 | K(-GkG-LPIFYPY)-EVN-Sta-VAEp-K(Chol'ester')-NH₂ x 3TFA | Lys(-Gly-DLys-Gly-Leu-Pro-Ile-Phe-Tyr-Pro-Tyr)-Glu-Val-Asn-Sta-Val-Ala-Glu-DPro-Lys(Chol'ester')-NH₂ x 3TFA | 3116.5 | 0.000043 |
| 63 | 63 | k(-GkG-LPIFYPY)-EVN-Sta-VAEp-K(Chol'ester')-NH₂ x 3TFA | DLys(-Gly-DLys-Gly-Leu-Pro-Ile-Phe-Tyr-Pro-Tyr)-Glu-Val-Asn-Sta-Val-Ala-Glu-DPro-Lys(Chol'ester')-NH₂ x 3TFA | 3116.5 | 0.000026 |
| 64 | 64 | YPKFIPL-GkG-EVN-MetSta-VAEP-K(Chol'ester')-NH₂ x 3TFA | Tyr-Pro-Lys-Phe-Ile-Pro-Leu-Gly-DLys-Gly-Glu-Val-Asn-MetSta-Val-Ala-Glu-Pro-Lys(Chol'ester')-NH₂ x 3TFA | 2971.4 | 0.000061 |

TABLE 2-continued

IC50 values of selected examples

| Ex. | SEQ ID NO: | Name | Systematic Name | MW | IC 50 (µM) |
|---|---|---|---|---|---|
| 65 | 65 | YPKFIPL-GkG-EVN-Leu*Ala-AEp-K(Chol'estert)-NH₂ x 3TFA | Tyr-Pro-Lys-Phe-Ile-Pro-Leu-Gly-DLys-Gly-Glu-Val-Asn-Leu*Ala-Ala-Glu-DPro-Lys(Chol'estert)-NH₂ x 3TFA | 2882.2 | 0.000039 |
| 66 | 66 | YPYFKPA-GkG-EVN-Sta-VAEp-K(Chol'estert)-NH₂ x 3TFA | Tyr-Pro-Tyr-Phe-Lys-Pro-Ala-Gly-DLys-Gly-Glu-Val-Asn-Sta-Val-Ala-Glu-DPro-Lys(Chol'estert)-NH₂ x 3TFA | 2961.3 | |
| 67 | 67 | TFKPANG-GkG-EVN-Sta-VAEp-K(Chol'estert)-NH₂ x 3TFA | Thr-Phe-Lys-Pro-Ala-Asn-Gly-Gly-DLys-Gly-Glu-Val-Asn-Sta-Val-Ala-Glu-DPro-Lys(Chol'estert)-NH₂ x 3TFA | 2810.1 | |
| 68 | 68 | GARFIPA-GkG-EVN-Sta-VAEp-K(Chol'estert)-NH₂ x 3TFA | Gly-Ala-Arg-Phe-Ile-Pro-Ala-Gly-DLys-Gly-Glu-Val-Asn-Sta-Val-Ala-Glu-DPro-Lys(Chol'estert)-NH₂ x 3TFA | 2807.1 | |
| 69 | 69 | YPKFIPA-GkG-EVN-Sta-VAEp-K(Chol'estert)-NH₂ x 3TFA | Tyr-Pro-Lys-Phe-Ile-Pro-Ala-Gly-DLys-Gly-Glu-Val-Asn-Sta-Val-Ala-Glu-DPro-Lys(Chol'estert)-NH₂ x 3TFA | 2911.2 | |
| 70 | 70 | YPKFISA-GkG-EVN-Sta-VAEp-K(Chol'estert)-NH₂ | Tyr-Pro-Lys-Phe-Ile-Ser-Ala-Gly-DLys-Gly-Glu-Val-Asn-Sta-Val-Ala-Glu-DPro-Lys (Chol'estert)-NH₂ x 3TFA | 2901.2 | |

Pharmaceutical Compositions

The dual-site BACE1 inhibitors and the pharmaceutically acceptable salts can be used as therapeutically active substances, e.g. in the form of pharmaceutical preparations. Examples for pharmaceutical preparations are an enteral formulation, e.g. in the form of tablets, coated tablets, dragées, hard and soft gelatine capsules, solutions, emulsions or suspensions or the like. The administration can, however, also be effected rectally, e.g. in the form of suppositories, parenterally, e.g. in the form of injection solutions, or as intranasal delivery, e.g. as nasal spray.

The dual-site BACE1 inhibitors and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like. The dual-site BACE1 inhibitors and the pharmaceutically acceptable salts thereof can also be encapsulated in suitable polymers or formulated using nanotechnology.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a dual-site BACE1 inhibitor or a pharmaceutically acceptable salt thereof and a therapeutically inert carrier are also an object of the present invention, as is a process for their production, which comprises bringing one or more dual-site BACE1 inhibitors and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a dual-site BACE1 inhibitors or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, preferably 1-100 mg, of a dual-site BACE1 inhibitor. Examples of compositions according to the invention are:

Example A

Tablets of the following composition are manufactured in the usual manner:

TABLE 3 possible tablet composition

| ingredient | mg/tablet | | | |
|---|---|---|---|---|
| | 5 | 25 | 100 | 500 |
| Dual-site BACE1 inhibitor | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1,2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 4 possible capsule ingredient composition

| ingredient | mg/capsule | | | |
|---|---|---|---|---|
| | 5 | 25 | 100 | 500 |
| Dual-site BACE1 inhibitor | 5 | 25 | 100 | 500 |
| Hydrous Lactose | 159 | 123 | 148 | — |
| Corn Starch | 25 | 35 | 40 | 70 |
| Talc | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The dual-site BACE1 inhibitor, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatine capsules.

Example B-2

Soft Gelatine Capsules of the following composition are manufactured:

TABLE 5 possible soft gelatine capsule ingredient composition

| ingredient | mg/capsule |
|---|---|
| Dual-site BACE1 inhibitor | 5 |
| Yellow wax | 8 |

TABLE 5-continued possible soft gelatine capsule ingredient composition

| ingredient | mg/capsule |
|---|---|
| Hydrogenated Soya bean oil | 8 |
| Partially hydrogenated plant oils | 34 |
| Soya bean oil | 110 |
| Total | 165 |

TABLE 6 possible soft gelatine capsule composition

| ingredient | mg/capsule |
|---|---|
| Gelatin | 75 |
| Glycerol 85% | 32 |
| Karion 83 | 8 (dry matter) |
| Titanium dioxide | 0.4 |
| Iron oxide yellow | 1.1 |
| Total | 116.5 |

Manufacturing Procedure

The dual-site BACE1 inhibitor is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 7 possible suppository composition

| ingredient | mg/supp. |
|---|---|
| Dual-site BACE1 inhibitor | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered dual-site BACE1 inhibitor is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 8 possible injection solution composition

| ingredient | mg/injection solution. |
|---|---|
| Dual-site BACE1 inhibitor | 3 |
| Polyethylene Glycol 400 | 150 |

TABLE 8-continued

| possible injection solution composition | |
| --- | --- |
| ingredient | mg/injection solution. |
| acetic acid | q.s. ad pH 5.0 |
| water for injection solutions | ad 1.0 ml |

Manufacturing Procedure

The dual-site BACE1 inhibitor is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 9

| possible sachet composition | |
| --- | --- |
| ingredient | mg/sachet |
| Dual-site BACE1 inhibitor | 50 |
| Lactose, fine powder | 1015 |
| Microcrystalline cellulose (AVICEL PH 102) | 1400 |
| Sodium carboxymethyl cellulose | 14 |
| Polyvinylpyrrolidone K 30 | 10 |
| Magnesium stearate | 10 |
| Flavoring additives | 1 |
| Total | 2500 |

Manufacturing Procedure

The dual-site BACE1 inhibitor is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

General Procedures for the CEM Liberty Microwave Peptide Synthesizer:

0.1 mMol scale:

Deprotection of Fmoc:

The washed and pre-swelled resin (435 mg, 0.1 mMol, TentaGel S RAM (Load: 0.23 mMol/g), (Rapp Polymere, Cat: S30023) was treated with a solution of piperidine 20% in DMF (7.0 mL) under microwave condition at 50° C. for 3 minutes for initial deprotection. The resin was washed with DMF and treated with a solution of piperidine 20% in DMF (7.0 mL) under microwave condition at 75° C. for 5 minutes for deprotection.

Coupling of Amino Acids:

To the washed and pre-swelled resin was added a solution of amino acid, 0.2M in DMF (2.5 mL, 5.0 eq.) followed by a solution of COMU 0.5 M in DMF (1.0 mL, 5.0 eq.), (CAS: 1075198-30-9, Iris Biotech, Cat: RL-1175.1000) followed by a solution of DIPEA 2M in NMP (0.5 mL, 10.0 eq.). This reaction mixture was treated under microwave condition at 75° C. for 5 minutes for coupling.

0.25 mMol Scale:

Deprotection of Fmoc:

The washed and pre-swelled resin (1.09 g, 0.25 mMol, TentaGel S RAM (Load: 0.23 mMol/g), (Rapp Polymere, Cat: S30023) was treated with a solution of piperidine 20% in DMF (10.0 mL) under microwave condition at 50° C. for 3 minutes for initial deprotection. The resin was washed with DMF and treated with a solution of piperidine 20% in DMF (10.0 mL) under microwave condition at 75° C. for 5 minutes for deprotection.

Coupling of Amino Acids:

To the washed and pre-swelled resin was added a solution of amino acid, 0.2M in DMF (5.0 mL, 4.0 eq.) followed by a solution of COMU 0.5M in DMF (2.0 mL, 4.0 eq.), (CAS: 1075198-30-9, Iris Biotech, Cat: RL-1175.1000) followed by a solution of DIPEA 2M in NMP (1.0 mL, 8.0 eq.). This reaction mixture was treated under microwave condition at 75° C. for 5 minutes for coupling.

General Procedure for MMT Cleavage:

0.1 mMol scale:

The MMT protected peptide on the resin was washed with CH2Cl2 and then treated with a solution of $CH_2Cl_2$:TFA:TIS 93:1:6 (5 mL) for 1 hour at room temperature on the shaker. The resin was washed with DMF for further coupling.

General Procedure for Coupling of "Chol":

1.0 mMol scale:

The deprotected, with DMF washed and preswelled resin was treated with a solution of Cholesteryl hydrogen succinate (2.43 g, 5.0 eq.), (CAS: 1510-21-0, Sigma-Aldrich, Cat: C6512) and COMU (2.14 g, 5.0 eq.), (CAS: 1075198-30-9, Iris Biotech, Cat: RL-1175.1000) and DIPEA (2.04 mL, 12.0 eq.) in 50 mL DMF for 1 hour at room temperature on the shaker.

General Procedure for Coupling of "Chol'Ether'":

0.1 mMol scale:

The deprotected, with DMF washed and pre-swelled resin was treated with a solution of Compound 8 (163 mg, 3.0 eq.) and COMU (128 mg, 3.0 eq.), (CAS: 1075198-30-9, Iris Biotech, Cat: RL-1175.1000) and DIPEA (102 uL, 6.0 eq.) in 5.0 mL DMF for 1 hour at room temperature on the shaker.

General Procedure for Coupling of "27-OH-Chol":

0.1 mMol scale:

The deprotected, with DMF washed and preswelled resin was treated with a solution of compound 4 (92.5 mg, 1.5 eq.) and COMU (64.2 mg, 1.5 eq.), (CAS: 1075198-30-9, Iris Biotech, Cat: RL-1175.1000) and DIPEA (68 uL, 4.0 eq.) in 5.0 mL DMF for 1 hour at room temperature on the shaker.

General Procedure for Final Cleavage:

0.1 mMol scale:

The resin was washed with CH2Cl2 and then treated with a solution of TFA:TIS:water 95:2.5:2.5 (5 mL) for 30 minutes at room temperature on the shaker. The resin was filtered. The crude peptide was precipitated with $Et_2O$ (35 mL). The suspension was centrifuged and the solvent was decanted. The solid was dissolved in acetonitrile and water and freeze-dried to get the crude peptide.

General Procedure for Purification:

The crude product was dissolved in acetonitrile and water (containing 0.1% TFA) and then purified by preparative HPLC. Column YMC-Actus Pro C8, 5 µm, 75×30 mm with a gradient of water (containing 0.1% TFA):acetonitrile 70:30 to 2:98 and with a flow of 30 mL/min.

Cholesteryl Hydrogen Succinate

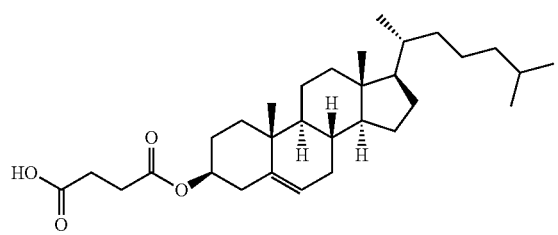

Commercial available: (CAS: 1510-21-0, Sigma-Aldrich, Cat: C6512)

Compound 4

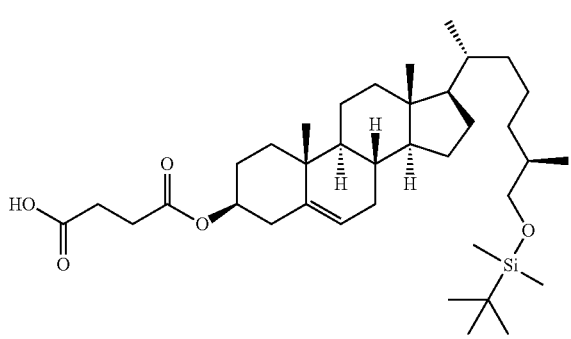

1

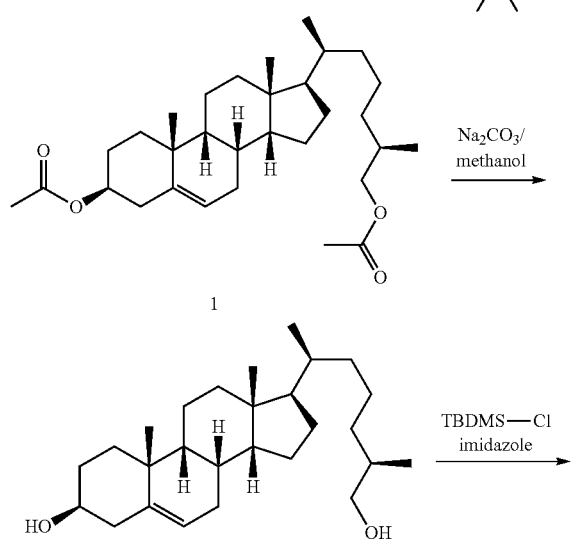

2

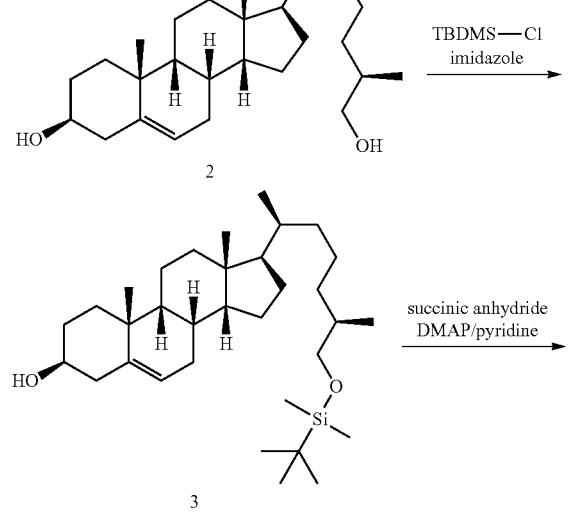

3

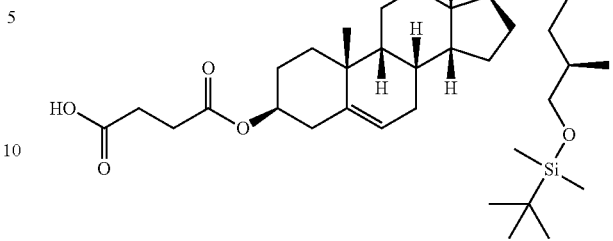

4

Synthesis of Title Compound 2:

To a solution of Compound (1) (650 mg, 1.34 mmol) in methanol (130 mL) was added sodium carbonate (283 mg, 2.67 mmol). The reaction mixture was stirred overnight at room temperature. TLC showed complete conversion. The reaction mixture was poured on 150 mL 10% aqueous NaHCO$_3$ solution and 150 mL CH$_2$Cl$_2$ and the layers were separated. The aqueous layer was extracted a second time with 100 mL CH$_2$Cl$_2$. The organic layers were washed with 150 mL brine, dried over MgSO$_4$, filtered and concentrated under vacuum. The residue was purified by silica gel chromatography on a 20 g column using an MPLC system (CombiFlash Companion, Isco Inc.) eluting with a gradient of n-heptane:ethyl acetate (100:0 to 30:70). White solid (475 mg, 88%). MS (ESI): m/z=402 [M].

Synthesis of Title Compound 3:

To a solution of (2) (470 mg, 1.17 mmol) in DMF (25 mL) was added imidazole (119 mg, 1.75 mmol) and TBDMS-Cl (229 mg, 1.52 mmol). The reaction mixture was stirred for 18 hours at room temperature. The reaction mixture was poured on 100 mL 10% aqueous citric acid solution and 100 mL CH$_2$Cl$_2$ and the layers were separated. The aqueous layer was extracted a second time with 100 mL CH$_2$Cl$_2$. The organic layers were washed with 50 mL brine, dried over MgSO$_4$, filtered and concentrated under vacuum. The residue was purified by silica gel chromatography on a 50 g column using an MPLC system (CombiFlash Companion, Isco Inc.) eluting with a gradient of n-heptane:ethyl acetate (100:0 to 30:70). White foam (396 mg, 66%). MS (EI): m/z=516 [M].

Synthesis of Title Compound 4:

To a solution of (3) (344 mg, 665 µmol) in chloroform (10 mL) and DMSO (1 mL) was added succinic anhydride (533 mg, 5.32 mmol) and DMAP (65.0 mg, 532 µmol) and pyridine (3.3 mL). The reaction mixture was stirred for 2 hours at 110° C. TLC showed complete conversion. The reaction mixture was poured on 50 mL 10% aqueous citric acid solution and 50 mL CH$_2$Cl$_2$ and the layers were separated. The aqueous layer was extracted a second time with 50 mL CH$_2$Cl$_2$. The organic layers were washed with 50 mL brine, dried over MgSO$_4$, filtered and concentrated under vacuum. The compound was purified by silica gel chromatography on a 50 g column using an MPLC system (CombiFlash Companion, Isco Inc.) eluting with a gradient of n-heptane:ethyl acetate (100:0 to 30:70). White solid (369 mg, 90%). MS (TurboSpray): m/z=615.5 [M−H]$^-$.

Compound 8

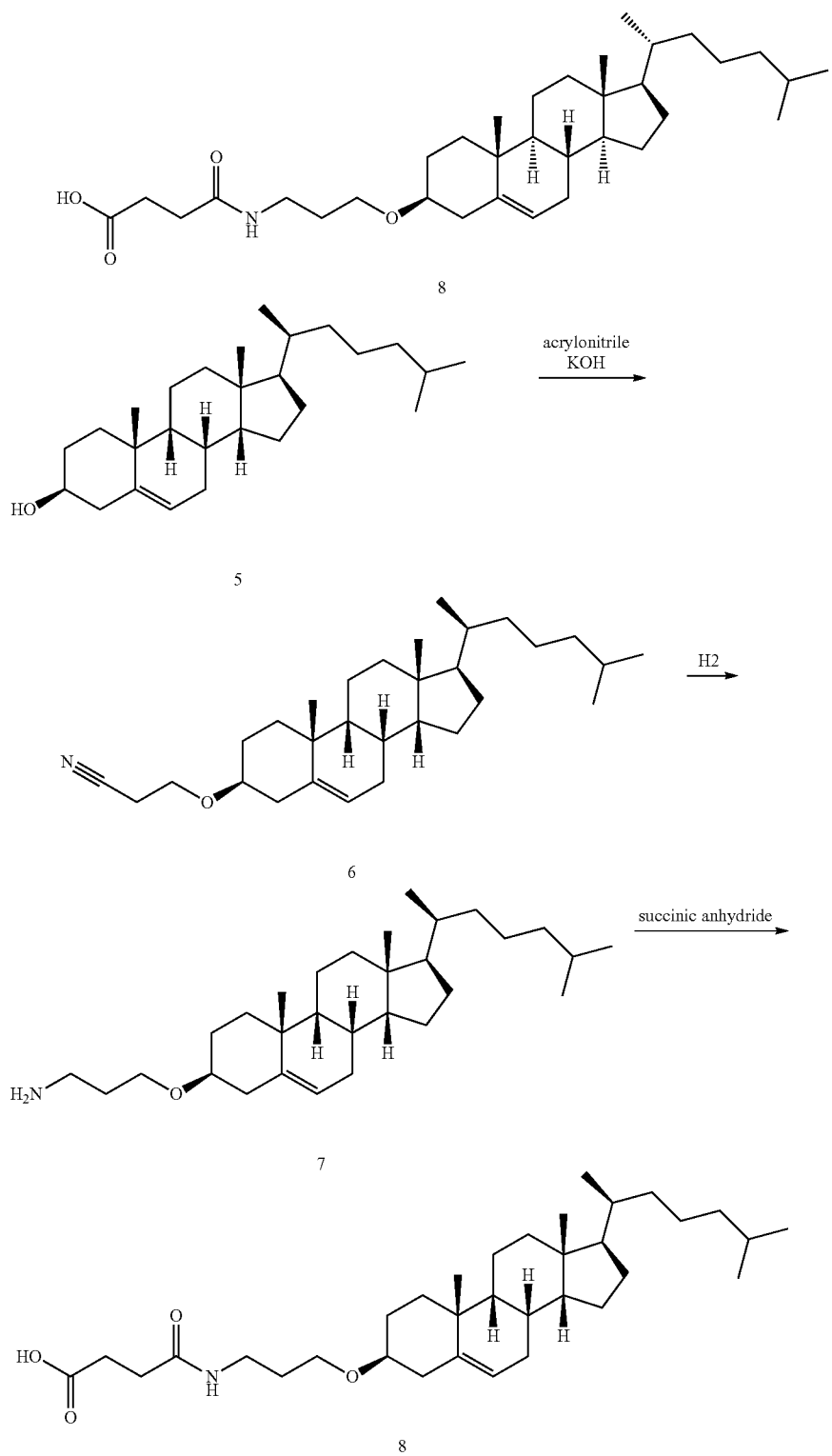

Synthesis of Title Compound 6:

To a solution of cholesterol (5) (10 g, 25.9 mmol, CAS: 57-88-5) in 1,4-dioxane (80 mL) was added a solution of KOH (319 mg, 5.69 mmol) in water (4.00 mL). A white suspension formed. Acrylonitrile (41.2 g, 776 mmol) was added dropwise over 10 minutes at room temperature. The reaction mixture was stirred for 5 days at room temperature. TLC showed complete conversion. The white suspension was filtered and washed with water. The filtrate was diluted with water. The formed suspension was again filtered and washed with water. The solid was combined and dried. White solid (11.67 g, 100%). MS (GC-EI-MS): m/z=439.4 [M+H]+

Synthesis of Title Compound 7:

To a solution of (6) (11.0 g, 25.0 mmol) in ethanol (444 mL) was added a solution of NaOH (111 mg, 2.78 mmol) in water (32 mL). Raney Nickel B113 ZNr313 (3.24 g, 25.7 mmol) was added under argon atmosphere. The vessel was closed and the reaction mixture was stirred under $H_2$-atmosphere at 40° C. at 3.5 bar for 3.5 hours. The reaction mixture was filtered and washed with ethanol. The filtrate was concentrated under vacuum. The residue was dissolved with 300 mL $CH_2Cl_2$ and 300 mL water and the layers were separated. The aqueous layer was extracted a second time with 200 mL $CH_2Cl_2$. The organic layers were washed with 200 mL brine, dried over $MgSO_4$, filtered and concentrated under vacuum. White solid (10.11 g, 91%). MS (EI): m/z=444.42 $[M+H]^+$ Synthesis of Title Compound 8:

To a suspension of (7) (10.11 g, 22.8 mmol) in ethyl acetate (375 mL) was added dropwise a solution of succinic anhydride (2.51 g, 25.1 mmol) in THF (18.8 mL) at room temperature. The pH was adjusted to pH 8.5 by adding DIPEA dropwise. The reaction mixture was stirred for 18 hours at room temperature. TLC ($CH_2Cl_2$:MeOH 4:1) showed complete conversion. The reaction mixture was concentrated under vacuum. The residue was dissolved with 300 mL $CH_2Cl_2$ and 300 mL 10% aqueous $KHSO_4$ and the layers were separated. The aqueous layer was extracted a second time with 200 mL $CH_2Cl_2$. The organic layers were washed with 200 mL brine, dried over $MgSO_4$, filtered and concentrated under vacuum. The light brown solid was suspended in diethyl ether, stirred for 1 hour and then filtered. White solid (7.98 g, 64%). MS (EI): m/z=544.44 [M+H]+

All examples described in table 1 can be prepared analogous to the general procedures described herein.

The invention claimed is:

1. A dual-site BACE1 inhibitor, or a pharmaceutically acceptable salt thereof, binding to both an enzymatic active site and a catalytic domain of the BACE1 enzyme, wherein an exosite inhibitory part (A') is connected to an active-site inhibitory part (B') of said dual-site BACE1 inhibitor by a linker (L'), and wherein B' is selected from the group consisting of:
   i. Glu-Val-Asn-Sta-Val-Ala-Glu-DPro-Lys(Chol)-NH$_2$ (SEQ ID NO: 96),
   ii. Glu-Val-Asn-Sta-Asp-Ala-Glu-DPro-Lys(Chol)-NH$_2$ (SEQ ID NO: 97),
   iii. Glu-Val-Asn-Sta-Val-Ala-Glu-DPro-Lys(27-OH-Chol)-NH$_2$ (SEQ ID NO: 100),
   iv. Glu-Val-Asn-Sta-Val-Ala-Glu-DPro-Lys(Chol-27-TFA-ester)-NH$_2$ (SEQ ID NO: 101),
   v. Glu-Val-Asn-Sta-Val-Ala-Glu-DPro-Lys(Chol'ester')-NH$_2$ (SEQ ID NO: 102),
   vi. Glu-Val-Asn-Sta-Val-Ala-Glu-Phe-Lys(Chol)-NH$_2$ (SEQ ID NO: 103),
   vii. Glu-Val-Asn-MetSta-Val-Ala-Glu-DPhe-Lys(Chol)-NH$_2$ (SEQ ID NO: 104),
   viii. Glu-Val-Asn-Leu*Ala-Ala-Glu-DPro-Lys(Chol)-NH$_2$ (SEQ ID NO: 106),
   ix. Glu-Val-Asn-Sta-Val-Ala-Glu-DPro-Lys(Chol'ether')-NH$_2$ (SEQ ID NO: 107),
   x. Leu-Pro-Ile-Phe-Tyr-Pro-Tyr-Glu-Val-Asn-Sta-Val-Ala-Glu-DPro-Lys(Chol'ester')-NH$_2$ (SEQ ID NO: 108),
   xi. Glu-Val-Asn-MetSta-Val-Ala-Glu-Pro-Lys(Chol'ester')-NH$_2$ (SEQ ID NO: 109), and
   xii. Glu-Val-Asn-Leu*Ala-Ala-Glu-DPro-Lys(Chol'ester')-NH$_2$ (SEQ ID NO: 110).

2. The dual-site BACE1 inhibitor according to claim 1, wherein L' is selected from the group consisting of:
   i. -(Gly)$_x$-, wherein x is 2, 3, 4, 5 or 6 (SEQ ID NO: 111),
   ii. —NH(CH$_2$)$_y$CO—, wherein y is 2, 4, 5 or 10,
   iii. PEG(3),
   iv. PEG(4),
   v. —X-Gly-Gly-, wherein X is selected from the group consisting of Ala, DAla, Ser, Lys and DLys,
   vi. -Gly-X-Gly-, wherein X is selected from the group consisting of Ala, DAla, Ser, Lys and DLys, and
   vii. -Gly-Gly-X—, wherein X is selected from the group consisting of Ala, DAla, Ser, Lys and DLys.

3. The dual-site BACE1 inhibitor according to claim 1, wherein A' is selected from the group consisting of:

i. Tyr-Pro-Tyr-Phe-Ile-Pro-Leu- (SEQ ID NO: 71),
ii. Ac-Tyr-Pro-Tyr-Phe-Ile-Pro-Leu- (SEQ ID NO: 72),
iii. Leu-Ile-Tyr-Phe-Pro-Tyr-Pro- (SEQ ID NO: 73),
iv. Tyr-Pro-Lys-Phe-Ile-Pro-Leu- (SEQ ID NO: 74),
v. Tyr-Pro-Tyr-Phe-Lys-Pro-Leu- (SEQ ID NO: 75),
vi. Tyr-Pro-Tyr-Phe-Ile-Lys-Leu- (SEQ ID NO: 76),
vii. Tyr-Pro-Lys-Phe-Lys-Pro-Leu-Gly- (SEQ ID NO: 77),
viii. Tyr-Pro-Lys-Phe-Ile-Lys-Leu- (SEQ ID NO: 78),
ix. Tyr-Pro-Lys-Phe-Lys-Lys-Leu- (SEQ ID NO: 79),
x. Lys-Pro-Tyr-Phe-Ile-Pro-Leu- (SEQ ID NO: 80),
xi. Tyr-Lys-Tyr-Phe-Ile-Pro-Leu- (SEQ ID NO: 81),
xii. Tyr-Pro-Tyr-Lys-Ile-Pro-Leu- (SEQ ID NO: 82),
xiii. Tyr-Pro-Tyr-Phe-Ile-Pro-Lys- (SEQ ID NO: 83),
xiv. DLys-Pro-Tyr-Phe-Ile-Pro-Leu- (SEQ ID NO: 84),
xv. Tyr-DLys-Tyr-Phe-Ile-Pro-Leu- (SEQ ID NO: 85),
xvi. Tyr-Pro-DLys-Phe-Ile-Pro-Leu- (SEQ ID NO: 86),
xvii. Tyr-Pro-Tyr-DLys-Ile-Pro-Leu- (SEQ ID NO: 87),
xviii. Tyr-Pro-Tyr-Phe-DLys-Pro-Leu- (SEQ ID NO: 88),
xix. Tyr-Pro-Tyr-Phe-Ile-DLys-Leu- (SEQ ID NO: 89),
xx. Tyr-Pro-Tyr-Phe-Ile-Pro-DLys- (SEQ ID NO: 90),
xxi. Lys,
xxii. DLys,
xxiii. Tyr-Pro-Tyr-Phe-Lys-Pro-Ala- (SEQ ID NO: 91),
xxiv. Thr-Phe-Lys-Pro-Ala-Asn-Gly- (SEQ ID NO: 92),
xxv. Gly-Ala-Arg-Phe-Ile-Pro-Ala- (SEQ ID NO: 93),
xxvi. Tyr-Pro-Lys-Phe-Ile-Pro-Ala- (SEQ ID NO: 94), and
xxvii. Tyr-Pro-Lys-Phe-Ile-Ser-Ala- (SEQ ID NO: 95).

4. A dual-site BACE1 inhibitor, selected from the group consisting of:
   Ac-Tyr-Pro-Tyr-Phe-Ile-Pro-Leu-Gly-Gly-Gly-Glu-Val-Asn-Sta-Val-Ala-Glu-DPro-Lys(Chol)-NH$_2$ (SEQ ID NO: 3),
   Ac-Tyr-Pro-Tyr-Phe-Ile-Pro-Leu-PEG(4)-Glu-Val-Asn-Sta-Val-Ala-Glu-DPro-Lys(Cho)-NH$_2$ (SEQ ID NOS 15 and 96),
   DLys-Pro-Tyr-Phe-Ile-Pro-Leu-Gly-DLys-Gly-Glu-Val-Asn-Sta-Val-Ala-Glu-DPro-Lys(Chol'ester')-NH$_2$ (SEQ ID NO: 55),
   DLys-Gly-DLys-Gly-Leu-Pro-Ile-Phe-Tyr-Pro-Tyr-Glu-Val-Asn-Sta-Val-Ala-Glu-DPro-Lys(Chol'ester')-NH$_2$ (SEQ ID NO: 63),
   Gly-Ala-Arg-Phe-Ile-Pro-Ala-Gly-DLys-Gly-Glu-Val-Asn-Sta-Val-Ala-Glu-DPro-Lys(Chol'ester')-NH$_2$ (SEQ ID NO: 68), Leu-Ile-Tyr-Phe-Pro-Tyr-Pro-Gly-Gly-Gly-Glu-Val-Asn-Sta-Val-Ala-Glu-DPro-Lys(Chol)-NH$_2$ (SEQ ID NO: 16), Leu-Ile-Tyr-Phe-Pwo-Tyr-Pro-Gly-Gly-Gily-Gly-Glu-Val-Asn-Sta-Val-Ala-Glu-DPro-Lys(Chol)-NH$_2$ (SEQ ID NO: 17), Lys-Pro-Tyr-Phe-Ile-Pro-Leu-Gly-DLys-Gly-Glu-Val-Asn-Sta-Val-Ala-Glu-DPro-Lys(Chol'ester')-NH$_2$ (SEQ ID NO: 48), Lys-Gly-DLys-Gly-Leu-Pro-Ile-Phe-Tyr-Pro-Tyr-Glu-Val-Asn-Sta-Val-Ala-Glu-DPro-Lys(Chol'ester')-NH$_2$ (SEQ ID NO: 62), Thr-Phe-Lys-Pro-Ala-Asn-Gly-Gly-DLys-Gly-Glu-Val-Asn-Sta-Val-Ala-Glu-DPro-Lys(Chol'ester')-NH$_2$ (SEQ ID NO: 67), Tyr-Pro-Tyr-Phe-Ile-Pro-Leu-Gly-Gly-Glu-Val-Asn-Sta-Val-Ala-Glu-DPro-Lys (Cho)-NH$_2$ (SEQ ID NO: 1), Tyr-Pro-Tyr-Phe-Ile-Pro-Leu-Gly-Gly-Gly-Glu-Val-Asn-Sta-Val-Ala-Glu-DPro-Lys(Chol)-NH$_2$ (SEQ ID NO: 2), Tyr-Pro-Tyr-Phe-Ile-Pro-Leu-Gly-Gly-Gly-Glu-Val-Asn-Sta-Asp-Ala-Glu-DPro-Lys(Chol)-NH$_2$ (SEQ ID NO: 4), Tyr-Pro-Tyr-Phe-Ile-Pro-Leu-Gly-Gly-Gly-Gly-Glu-Val-Asn-Sta-Val-Ala-Glu-DPro-Lys(Chol)-NH$_2$ (SEQ ID NO: 5), Tyr-Pro-Tyr-Ph-Ile-Pro-Lu-Gly-Gly-Gly-Gly-Glu-Val-Asn-Sta-Asp-Ala-Glu-DPro-Lys(Chol)-NH$_2$ (SEQ ID NO: 6), Tyr-Pro-Tyr-Phe-Ile-Pro-Leu-Gly-Gly-Gly-Gly-Glu-Val-Asn-Sta-Val-Ala-Glu-DPro-Lys(Chol)-NH$_2$ (SEQ ID NO: 7), Tyr-Pro-Tyr-Phe-Ile-Pro-Leu-Gly-Gly-Gly-Gly-Gly-Glu-Val-Asn-Sta-Val-Ala-Glu-DPro-Lys(Chol)-NH$_2$ (SEQ ID NO: 12), Tyr-Pro-Tyr-Phe-Ile-Pro-Leu-PEG(3)-Glu-Val-Asn-Sta-Val-Ala-Glu-DPro-Lys(Chol)-NH$_2$ (SEQ ID NOS 13 and 96), Tyr-Pro-Tyr-Phe-Ile-Pro-Leu-PEG(4)-Glu-Val-Asn-Sta-Val-Ala-Glu-DPro-Lys(Chol)-NH$_2$ (SEQ ID NOS 14 and 96), Tyr-Pro-Tyr-Phe-Ile-Pro-Leu-Gly-Gly-Gly-Glu-Val-Asn-Sta-Val-Ala-Glu-DPro-Lys(27-OH-Chol)-NH$_2$ (SEQ ID NO: 20), Tyr-Pro-Tyr-Phe-Ile-Pro-Leu-Gly-DLys-Gly-Glu-Val-Asn-Sta-Val-Ala-Glu-DPro-Lys(Chol-27-TFA-ester)-NH$_2$ (SEQ ID NO: 21), Tyr-Pro-Ty-Phe-Ile-Pro-Leu-ly-Ly-Gly-Glu-Val-Asn-Sta-Val-Ala-Glu-DPro-(Chol-27-Lys(Chol'ester')-NH$_2$ (SEQ ID NO: 22), Tyr-Pro-Tyr-Phe-Ile-Pro-Leu-NH(CH2)2CO-Glu-Val-Asn-Sta-Val-Ala-Glu-DPro-Lys(Chol)-NH$_2$ (SEQ ID NOS 8 and 96), Tyr-Pro-Tyr-Phe-Ile-Pro-Leu-NH(CH2)4CO-Glu-Val-Asn-Sta-Val-Ala-Glu-DPro-Lys(Chol)-NH$_2$ (SEQ ID NOS 9 and 96), Tyr-Pro-Tyr-Phe-Ile-r-Leu-N H(CH2)5CO-Glu-Val-Asn-Sta-Val-Ala-Glu-DPro-Lys(Chol)-NH$_2$ (SEQ ID NOS 10 and 96), Tyr-Pro-Tyr-Phe-Ile-Pro-Leu-NH(CH2)10CO-Glu-Val-Asn-Sta-Val-Ala-Glu-DPro-Lys(Chol)-NH$_2$ (SEQ ID NOS 11 and 96), Tyr-Pro-Tyr-Phe-Ile-Pro-Leu-Gly-Gly-Gly-Glu-Val-Asn-Sta-Val-Ala-Glu-DPro-Lys(Chol)-NH$_2$ (SEQ ID NO: 23), Tyr-Pro-Tyr-Phe-Ile-Pro-Leu-Gly-Gly-Gly-Glu-Val-Asn-MetSta-Val-Ala-Glu-DPhe-Lys(Chol)-NH$_2$ (SEQ ID NO: 24), Tyr-Pro-Tyr-Phe-fle-Pro-Leu-Gly-Gly-Gly-Gly-Gly-Glu-Val-Asn-MetSta-Val-Ala-Glu-DPhe-Lys(Chol)-NH$_2$ (SEQ ID NO: 25), Tyr-Pro-Tyr-Phe-Ile-Pro-Leu-PEG(3)-Glu-Val-Asn-Met-Sta-Val-Ala-Glu-DPhe-Lys(Chol)-NH$_2$ (SEQ ID NOS 26 and 104), Tyr-Pro-Tyr-Phe-Ile-Pro-Leu-PEG(4)-Glu-Val-Asn-Met-Sta-Val-Ala-Glu-DPhe-Lys(Cho)-NH$_2$ (SEQ ID NOS 27 and 104), Tyr-Pro-Tyr-Phe-Ile-Pro-Leu-Gly-Gly-Gly-Glu-Val-Asn-Leu*Ala-Ala-Glu-DPro-Lys(Chol)-NH$_2$ (SEQ ID NO: 29), Tyr-DLys-Tyr-Phe-Ile-Leu-Gly-Lys-Gly-Glu-Val-Asn-Sta-Val-Ala-Glu-DPro-Lys(Chol'ether')-NH$_2$ (SEQ ID NO: 30), Tyr-Lys-Tyr-Pe-Ile-Pro-Leu-Gly-DLys-Gly-Glu-Val-Asn-Sta-Val-Ala-Glu-DPro-Lys(Chol'ester')-NH$_2$ (SEQ ID NO: 56), Tyr-Pro-DLy-Pe-Ile-Pro-Leu-Gly-DLys-Gly-Glu-Val-Asn-Sta-Val-Ala-Glu-DPro-Lys(Chol'ester')-NH$_2$ (SEQ ID NO: 49), Tyr-Lys-Tyr-Pe-Ile-Pro-Leu-Gly-DLys-Gly-Glu-Val-Asn-Sta-Val-Ala-Glu-DPro-Lys(Chol'ester')-NH$_2$ (SEQ ID NO: 57), Tyr-Pro-Lys-Phe-Ile-ys-Leu-Gly-DLys-Gly-Glu-Val-Asn-Sta-Val-Ala-Glu-DPro-Lys(Chol)-NH$_2$ (SEQ ID NO: 46), Tyr-Pro-Lys-Phe-Ile-Pro-Ala-Gly-DLys-Gly-Glu-Val-Asn-Sta-Val-Ala-Glu-DPro-Lys(Chol'ester')-NH$_2$ (SEQ ID NO: 69), Tyr-Pro-Lys-Phe-Ile-Pro-Leu-Gly-DLys-Gly-Glu-Val-Asn-Leu*Ala-Ala-Glu-DPro-Lys(Chol'ester')-NH$_2$ (SEQ ID NO: 65), Tyr-Pro-Lys-Phe-Ile-Pro-Leu-Gly-DLys-Gly-Glu-Val-Asn-MetSta-Val-Ala-Glu-Pro-Lys(Chol'ester')-NH$_2$ (SEQ ID NO: 64), Tyr-Pro-Lys-Phe-Ile-Pro-Leu-Gly-DLys-Gly-lu-Val-Asn-Sta-Val-Ala-Glu-DPro-Lys(Chol)-NH$_2$ (SEQ ID NO: 36), Tyr-Pro-Lys-Phe-Ile-Pro-Leu-Gly-DLys-Gly-Glu-Val-Asn-Sta-Val-Ala-Glu-DPro-Lys(Chol'ether')-NH$_2$ (SEQ ID NO: 44), Tyr-Pro-Lys-Phe-Ile-Pro-Leu-Gly-Gly-Gly-Glu-Val-Asn-Sta-Val-Ala-Glu-DPro-Lys(Chol)-NH$_2$ (SEQ ID NO: 31), Tyr-Pro-Lys-Phe-Ile-Ser-Ala-Gly-DLys-Gly-Glu-Val-Asn-Sta-Val-Ala-Glu-DPro-Lys(Chol'ester')-NH$_2$ (SEQ ID NO: 70), Tyr-Pro-Lys-Phe-Lys-Lys-Leu-Gly-DLys-Gly-Glu-Val-Asn-Sta-Val-Ala-Glu-DPro-Lys(Chol)-NH$_2$ (SEQ ID NO: 47), Tyr-Pro-Lys-Phc-Lys-Pro-Lcu-Gly-DLys-Gly-Glu-Val-Asn-Sta-Val-Ala-Glu-DPro-Lys(Chol)-NH$_2$ (SEQ ID NO: 45), Tyr-Pro-Tyr-DLys-Ile-Pro-Leu-Gly-DLys-Gly-Glu-Val-Asn-Sta-Val-Ala-Glu-DPro-Lys(Chol'ester')-NH$_2$ (SEQ ID NO: 58), Tyr-Pro-Tyr-Lys-Ile-Pro-Leu-Gly-DLys-Gly-Glu-Val-Asn-Sta-Val-Ala-Glu-DPro-Lys(Chol'ester')-NH$_2$ (SEQ ID NO: 50), Tyr-Pro-Tyr-Phe-DLys-Pro-Lcu-Gly-DLys-Gly-Glu-Val-Asn-Sta-Val-Ala-Glu-DPro-Lys(Chol'ester')-NH$_2$ (SEQ ID NO: 59), Tyr-Pro-Tyr-Phe-Ile-DLys-Leu-Gly-DLys-Gly-Glu-Val-Asn-Sta-Val-Ala-Glu-DPro-Lys(Chol'ester')-NH$_2$ (SEQ ID NO: 60),
Tyr-Pro-Tyr-Phe-Ile-Lys-Leu-Gly-DLys-Gly-Glu-Val-Asn-Sta-Val-Ala-Glu-DPro-Lys(Chol)-NH$_2$ (SEQ ID NO: 38),
Tyr-Pro-Tyr-Phe-Ile-Lys-Leu-Gly-Gly-Gly-Glu-Val-Asn-Sta-Val-Ala-Glu-DPro-Lys(Chol)-NH$_2$ (SEQ ID NO: 33),
Tyr-Pro-Tyr-Phe-Ile-Lys-Leu-PEG(4)-Glu-Val-Asn-Sta-Val-Ala-Glu-DPro-Lys(Chol)-NH$_2$ (SEQ ID NOS 35 and 96),
Tyr-Pro-Tyr-Phe-Ile-Pro-DLys-Gly-DLys-Gly-Glu-Val-Asn-Sta-Val-Ala-Glu-DPro-Lys(Chol'ester')-NH$_2$ (SEQ ID NO: 61),
Tyr-Pro-Tyr-Phe-Ile-Pro-Leu-DAla-Gly-Gly-Glu-Val-Asn-Sta-Val-Ala-Glu-DPro-Lys(Chol'ester')-NH$_2$ (SEQ ID NO: 52),
Tyr-Pro-Tyr-Phe-Ile-Pro-Leu-DLys-Gly-Gly-Glu-Val-Asn-Sta-Val-Ala-Glu-DPro-Lys(Chol)-NH$_2$ (SEQ ID NO: 41),
Tyr-Pro-Tyr-Phe-Ile-Pro-Leu-Gly-DAla-Gly-Glu-Val-Asn-Sta-Val-Ala-Glu-DPro-Lys(Chol'ester')-NH$_2$ (SEQ ID NO: 53),
Tyr-Pro-Tyr-Phe-Ile-ProLu-Gly-Gly-DLys-Glu-Val-Asn-Sta-Val-Ala-Glu-DPro-Lys(Chol)-NH$_2$ (SEQ ID NO: 43),
Tyr-Pro-Tyr-Phe-Ile-Pro-Leu-Gly-Lys-Glu-Val-Asn-Sta-Val-Ala-Glu-DPro-Lys(Chol)-NH$_2$ (SEQ ID NO: 42),
Tyr-Pro-Tyr-Phe-Ile-Pro-Leu-Gly-Lys-Gly-Glu-Val-Asn-Sta-Val-Ala-Glu-DPro-Lys(Chol)-NH$_2$ (SEQ ID NO: 39),
Tyr-Pro-Tyr-Phe-Ile-Pro-Lcu-Lys-Gly-Gly-Glu-Val-Asn-Sta-Val-Ala-Glu-DPro-Lys(Chol)-NH$_2$ (SEQ ID NO: 40),
Tyr-Pro-Tyr-Phe-Ile-Pro-Lcu-Scr-Gly-Gly-Glu-Val-Asn-Sta-Val-Ala-Glu-DPro-Lys(Chol'ester')-NH$_2$ (SEQ ID NO: 54),
Tyr-Pro-Tyr-Phe-fle-Pro-Lys-Gly-DLys-Gly-Glu-Val-Asn-Sta-Val-Ala-Glu-DPro-Lys(Chol'ester')-NH$_2$ (SEQ ID NO: 51),
Tyr-Pro-Tyr-Phe-Lys-Pro-Ala-Gly-DLys-Gly-Glu-Val-Asn-Sta-Val-Ala-Glu-DPro-Lys(Chol'ester')-NH$_2$ (SEQ II) NO: 66),
Tyr-Pro-Tyr-Phe-Lys-Pro-Leu-Gly-DLys-Gly-Glu-Val-Asn-Sta-Val-Ala-Glu-DPro-Lys(Chol)-NH$_2$ (SEQ ID NO: 37),
Tyr-Pro-Tyr-Phe-Lys-Pro-Leu-Gly-Gly-Gly-Glu-Val-Asn-Sta-Val-Ala-Glu-DPro-Lys(Chol)-NH$_2$ (SEQ ID NO: 32), and
Tyr-Pro-Tyr-Phe-Lys-Pro-Leu-PEG(4)-Glu-Val-Asn-Sta-Val-Ala-Glu-DPro-Lys(Chol)-NH$_2$ (SEQ ID NOS 34 and 96),
or a pharmaceutically acceptable salt thereof.

5. The dual-site BACE1 inhibitor according to claim 4, wherein the pharmaceutically acceptable salt is trifluoroacetate.

6. A pharmaceutical composition, comprising a dual-site BACE1 inhibitor according to claim 1, or a pharmaceutically acceptable salt thereof, and a pharmaceutically acceptable carrier and/or a pharmaceutically acceptable auxiliary substance.

7. A method of inhibiting BACE1 activity, comprising the step of administering a dual-site BACE1 inhibitor according to claim 1 to a human being or animal in need thereof.

8. A method of treating a disease or disorder characterized by elevated β-amyloid levels and/or β-amyloid oligomers and/or β-amyloid plaques, comprising the step of administering a dual-site BACE1 inhibitor according to claim 1, or a pharmaceutically acceptable salt thereof, to a human being or animal in need thereof, wherein said disease or disorder is Alzheimer's disease or type 2 diabetes.

9. A method of treating Alzheimer's disease, comprising the step of administering a dual-site BACE1 inhibitor according to claim 1, or a pharmaceutically acceptable salt thereof, to a human being or animal in need thereof.

10. A method of treating diabetes, comprising the step of administering a dual-site BACE1 inhibitor according to claim 1, or a pharmaceutically acceptable salt thereof, to a human being or animal in need thereof, wherein said diabetes is type 2 diabetes.

11. A pharmaceutical composition, comprising a dual-site BACE1 inhibitor according to claim 4, or a pharmaceutically acceptable salt thereof, and a pharmaceutically acceptable carrier and/or a pharmaceutically acceptable auxiliary substance.

12. A method of inhibiting BACE1 activity, comprising the step of administering a dual-site BACE1 inhibitor according to claim 4, or a pharmaceutically acceptable salt thereof, to a human being or animal in need thereof.

13. A method of treating a disease or disorder characterized by elevated β-amyloid levels and/or β-amyloid oligomers and/or β-amyloid plaques, comprising the step of administering a dual-site BACE1 inhibitor according to claim 4, or a pharmaceutically acceptable salt thereof, to a human being or animal in need thereof, wherein said disease or disorder is Alzheimer's disease or type 2 diabetes.

14. A method of treating Alzheimer's disease, comprising the step of administering a dual-site BACE1 inhibitor according to claim 4, or a pharmaceutically acceptable salt thereof, to a human being or animal in need thereof.

15. A method of treating type 2 diabetes, comprising the step of administering a dual-site BACE1 inhibitor according to claim 4, or a pharmaceutically acceptable salt thereof, to a human being or animal in need thereof.

* * * * *